(12) United States Patent
Zachar

(10) Patent No.: US 10,744,287 B2
(45) Date of Patent: Aug. 18, 2020

(54) LARYNGEAL MASK CUFFS

(71) Applicant: AIRWAY MEDIX S.A., Warsaw (PL)

(72) Inventor: Oron Zachar, Tel Aviv (IL)

(73) Assignee: AIRWAY MEDIX S.A., Warsaw (PL)

( * ) Notice: Subject to any disclaimer, the term of this patent is extended or adjusted under 35 U.S.C. 154(b) by 0 days.

(21) Appl. No.: 16/423,974

(22) Filed: May 28, 2019

(65) Prior Publication Data

US 2019/0282774 A1 Sep. 19, 2019

Related U.S. Application Data

(63) Continuation of application No. PCT/IL2019/050405, filed on Apr. 11, 2019, which is a continuation-in-part of application No. PCT/IL2018/051306, filed on Nov. 29, 2018, said application No. PCT/IL2018/051306 is a continuation-in-part of application No. 15/951,564, filed on Apr. 12, 2018, now Pat. No. 10,173,022, and
(Continued)

(51) Int. Cl.
*A61M 16/04* (2006.01)

(52) U.S. Cl.
CPC ...... *A61M 16/045* (2014.02); *A61M 16/0445* (2014.02); *A61M 16/0463* (2013.01); *A61M 16/0488* (2013.01)

(58) Field of Classification Search
None
See application file for complete search history.

(56) References Cited

U.S. PATENT DOCUMENTS

| 3,599,620 A | 8/1971 | Balin |
| 4,119,101 A | 10/1978 | Igich |

(Continued)

FOREIGN PATENT DOCUMENTS

| CN | 106823086 | 6/2017 |
| EP | 0922465 | 6/1999 |

(Continued)

OTHER PUBLICATIONS

An International Search Report (ISR) and Written Opinion issued in the parent application, PCT/IL2019/050405, dated Jul. 15, 2019.
(Continued)

*Primary Examiner* — Rachel T Sippel
(74) *Attorney, Agent, or Firm* — Sughrue Mion, PLLC

(57) ABSTRACT

A laryngeal mask airway (LMA) device includes a backplate, an inflatable balloon, an airway tube, and a non-inflatable skeleton, which extends anteriorly from the backplate, and which is shaped so as to define a skeleton anterior side that has a pre-formed shape. A distal end of an inflation tube is coupled in fluid communication with (i) an interior of the inflatable balloon for supplying air to the inflatable balloon, and (ii) at least a portion of the skeleton anterior side. The inflatable balloon is shaped so as to define an inflatable annular cuff which (a) covers at least a portion of the skeleton anterior side, and (b) has a cuff anterior side that is configured to form a seal around a laryngeal inlet of a patient when the inflatable annular cuff is disposed at an LMA-insertion location within a throat of the patient. Other embodiments are also described.

27 Claims, 20 Drawing Sheets

Related U.S. Application Data a continuation-in-part of application No. 15/878,993, filed on Jan. 24, 2018, now Pat. No. 10,369,311.

(60) Provisional application No. 62/789,208, filed on Jan. 7, 2019, provisional application No. 62/592,020, filed on Nov. 29, 2017.

(56) References Cited

U.S. PATENT DOCUMENTS

| | | | |
|---|---|---|---|
| 4,134,407 A | | 1/1979 | Elam |
| 5,007,919 A | | 4/1991 | Silva et al. |
| 5,255,670 A | | 10/1993 | Lomholt |
| 5,632,271 A | | 5/1997 | Brain |
| 5,871,012 A | * | 2/1999 | Neame .................. A61M 16/04 128/201.26 |
| 5,983,897 A | * | 11/1999 | Pagan ............... A61M 16/0409 128/200.26 |
| 6,439,232 B1 | | 8/2002 | Brain |
| 6,526,977 B1 | | 3/2003 | Gobel |
| 7,305,985 B2 | | 12/2007 | Brain |
| 8,783,256 B2 | | 7/2014 | Brain |
| 10,173,022 B1 | | 1/2019 | Zachar |
| 10,441,735 B1 | * | 10/2019 | Zhou ................. A61M 16/0057 |
| 2003/0037790 A1 | | 2/2003 | Brain |
| 2006/0027238 A1 | | 2/2006 | Lin |
| 2008/0078403 A1 | | 4/2008 | Clayton |
| 2009/0120445 A1 | | 5/2009 | Chikashige |
| 2012/0145160 A1 | | 6/2012 | Brain |
| 2013/0060212 A1 | * | 3/2013 | Hanuka .................. A61F 5/445 604/333 |
| 2013/0220332 A1 | * | 8/2013 | Baska .................. A61M 16/04 128/207.15 |
| 2014/0076309 A1 | | 3/2014 | Takeda et al. |
| 2015/0114400 A1 | | 4/2015 | Dubach |
| 2015/0283343 A1 | | 10/2015 | Schnell et al. |
| 2015/0290410 A1 | | 10/2015 | Schnell et al. |
| 2016/0158040 A1 | | 6/2016 | Zupkofska |
| 2016/0346493 A1 | * | 12/2016 | Wight ............... A61M 16/0409 |
| 2019/0160243 A1 | | 5/2019 | Zachar |

FOREIGN PATENT DOCUMENTS

| | | |
|---|---|---|
| GB | 2324735 | 6/2001 |
| WO | 2008/038430 | 4/2008 |
| WO | 2015/015233 | 2/2015 |
| WO | 2017/153988 | 9/2017 |
| WO | 2018/045555 | 3/2018 |

OTHER PUBLICATIONS

Legend M.D. product catalog excerpts 2007.
Ambu AuraOnce AuraStraight brochure Feb. 2009.
Rokamp KZ et al, "Tracheal tube and laryngeal mask cuff pressure during anaesthesia—mandatory monitoring is in need," BMC Anesthesiology, Dec. 2010 (text only).
Teleflex EMS-LMA-Airways-Quick-Reference-Guide 2013.
Teleflex LMA-TF-Supreme brochure Mar. 2014.
Two-balloon experiment—Wikipedia downloaded Jan. 22, 2018.
U.S. Appl. No. 62/789,208, filed Jan. 7, 2019.
An Office Action dated Jul. 11, 2018, which issued during the prosecution of U.S. Appl. No. 15/951,564.
An Office Action dated Jul. 6, 2018, which issued during the prosecution of U.S. Appl. No. 15/878,993.
U.S. Appl. No. 62/592,020, filed Nov. 29, 2017.
An Office Action dated Jan. 14, 2019, which issued during the prosecution of U.S. Appl. No. 16/160,668.
Notice of Allowance dated Mar. 4, 2019, which issued during the prosecution of U.S. Appl. No. 16/160,668.
Notice of Allowance dated Apr. 3, 2019, which issued during the prosecution of U.S. Appl. No. 15/878,993.
An International Search Report and a Written Opinion both dated Feb. 22, 2019, which issued during the prosecution of Applicant's PCT/IL2018/051306.
An Office Action dated May 2, 2018, which issued during the prosecution of U.S. Appl. No. 15/878,993.
Notice of Allowance dated Nov. 13, 2018, which issued during the prosecution of U.S. Appl. No. 15/951,564.

* cited by examiner

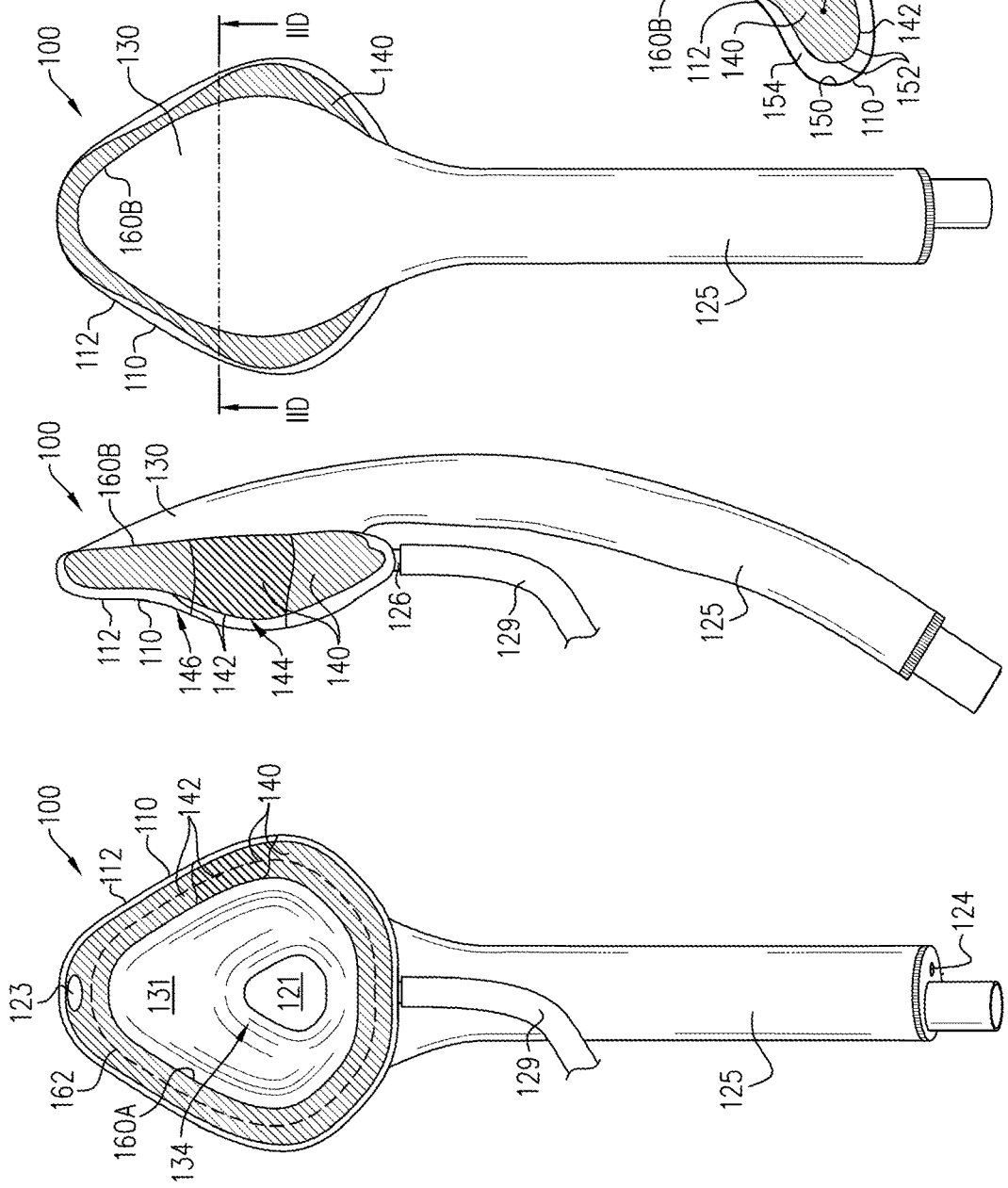

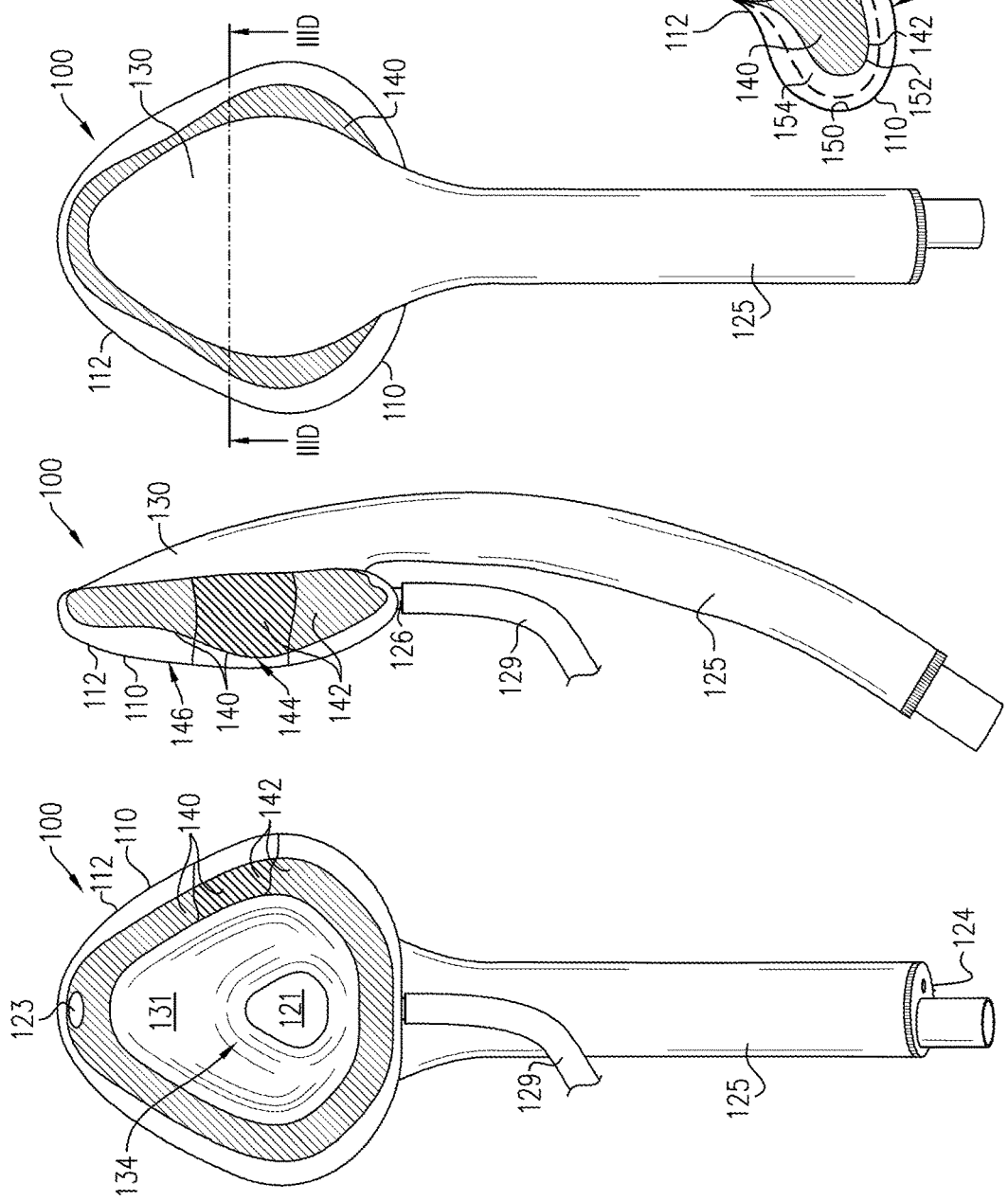

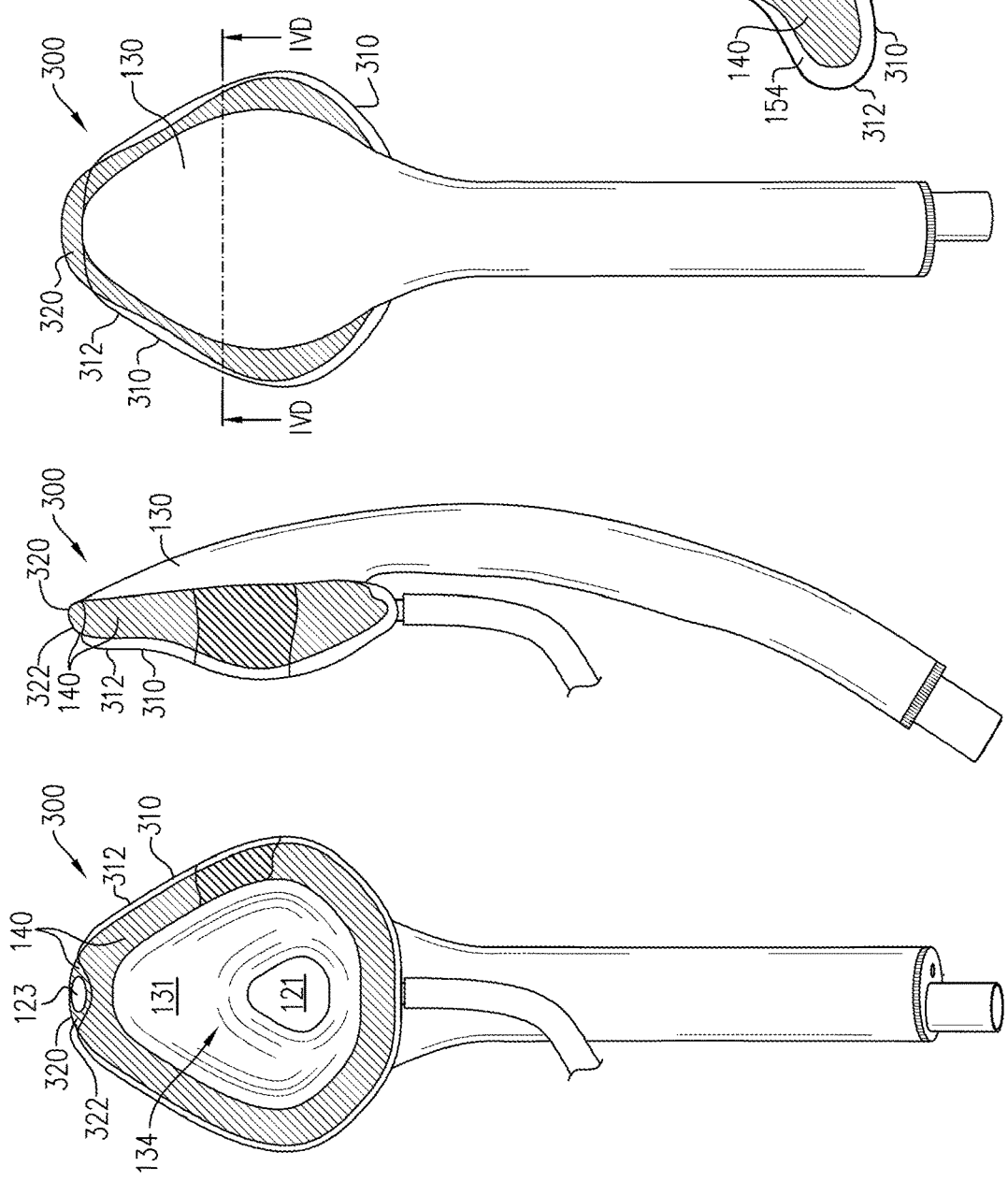

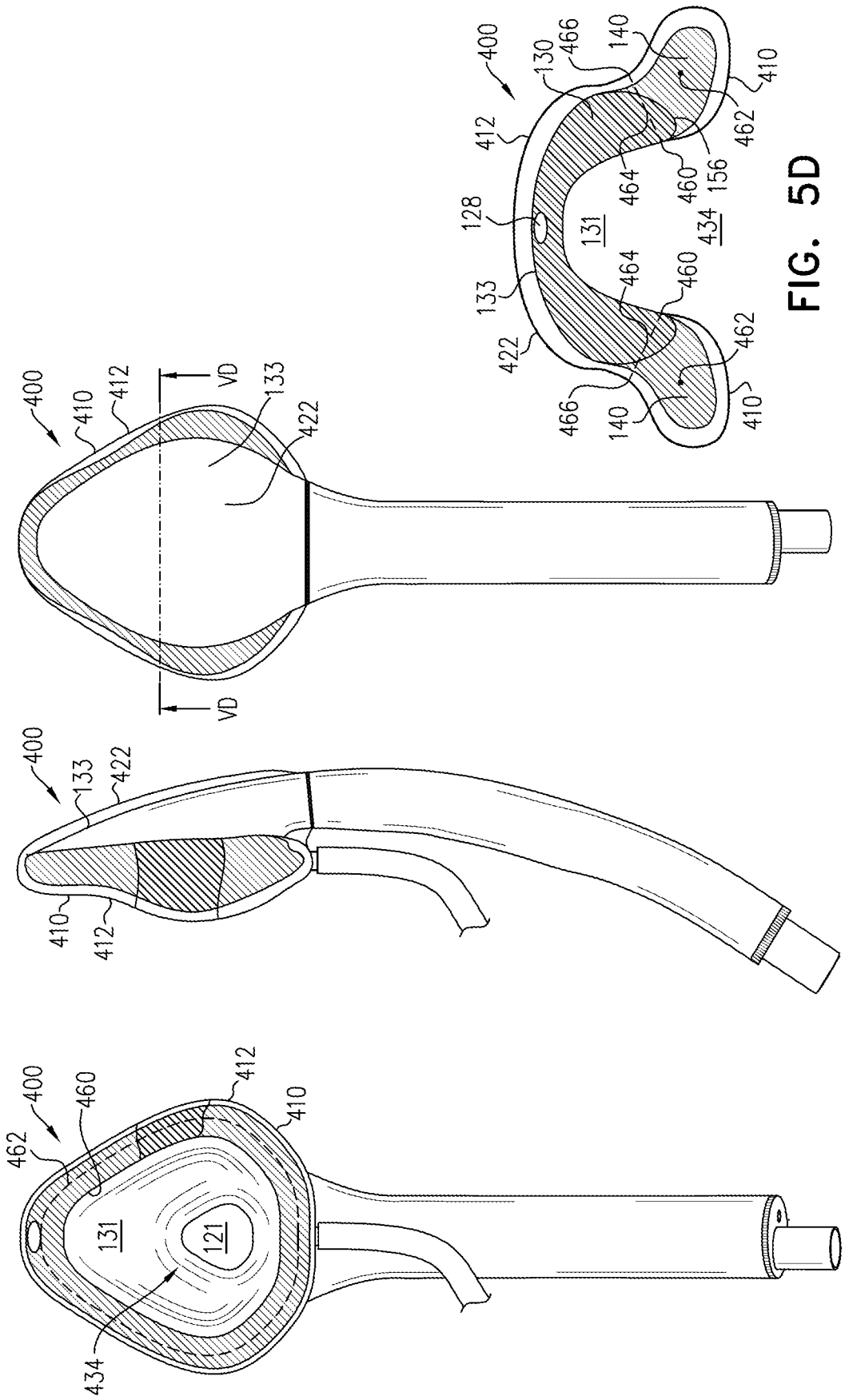

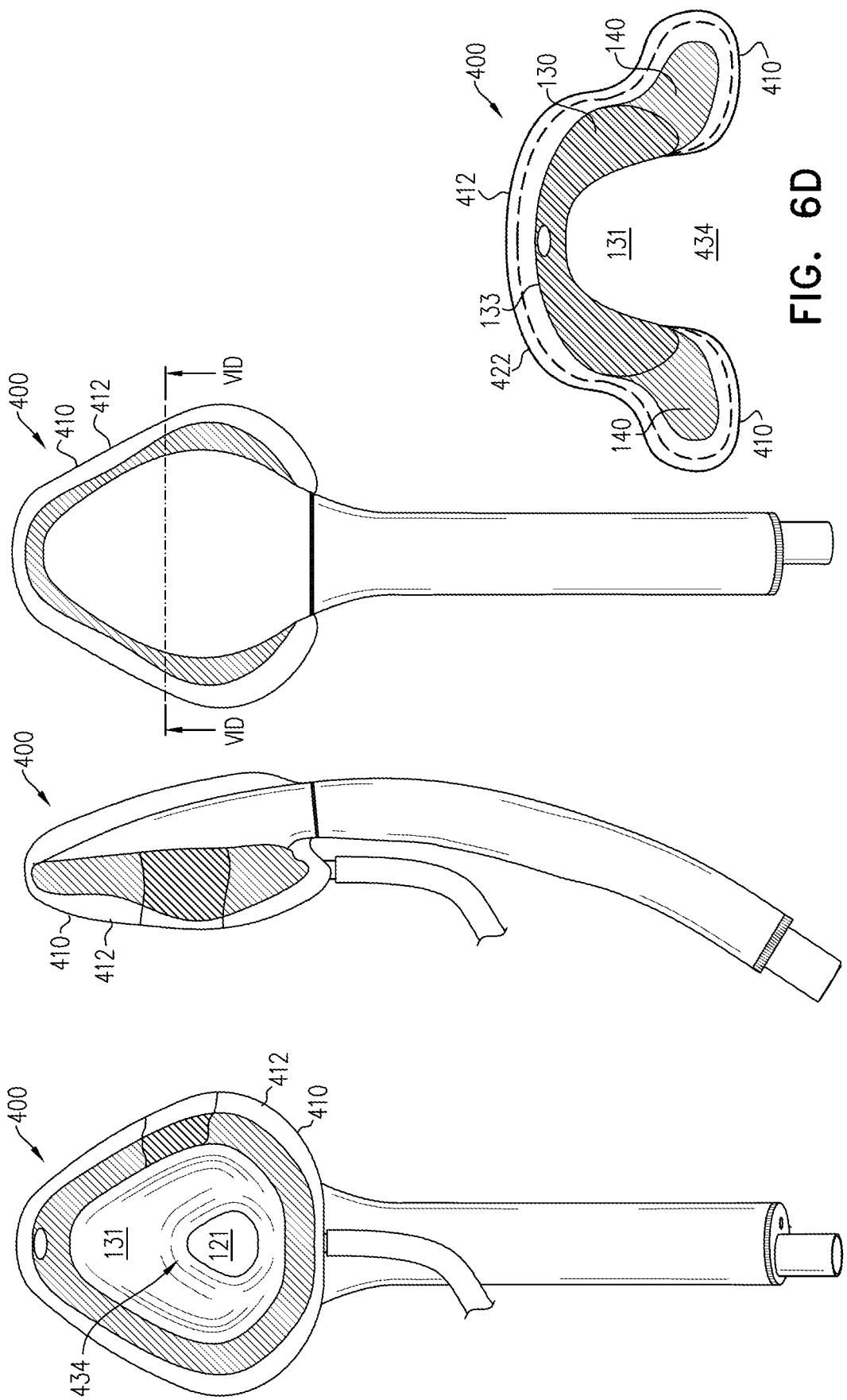

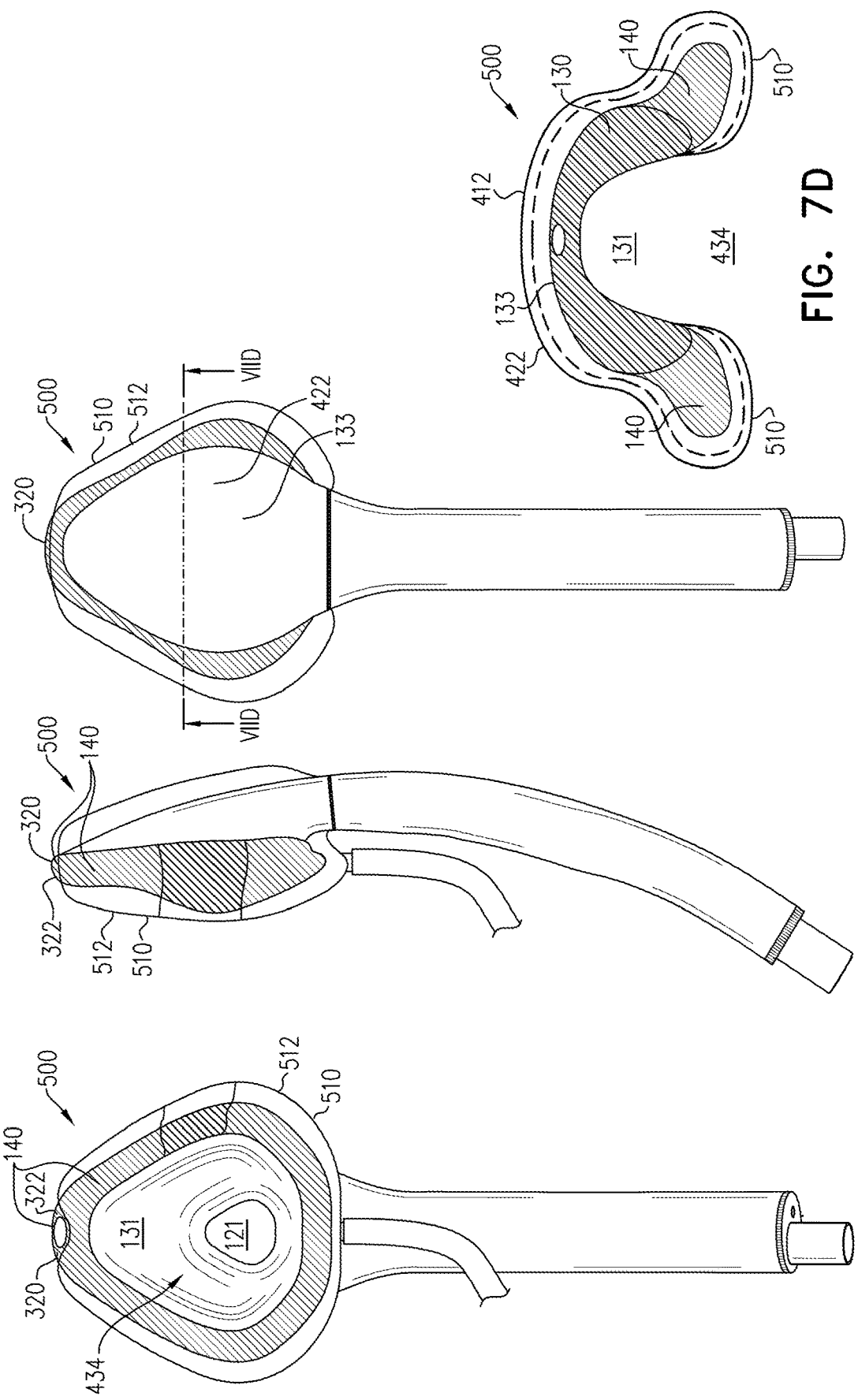

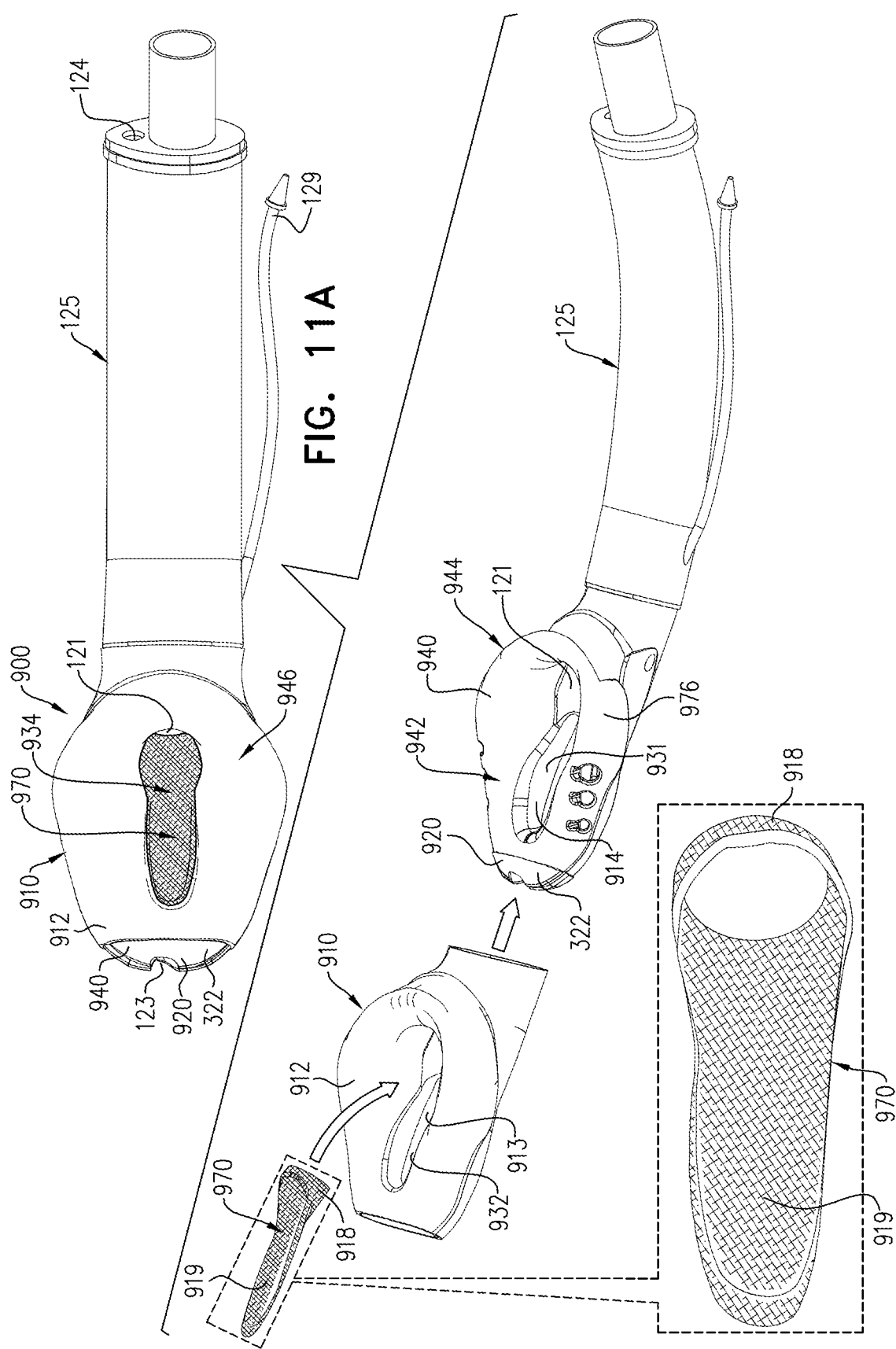

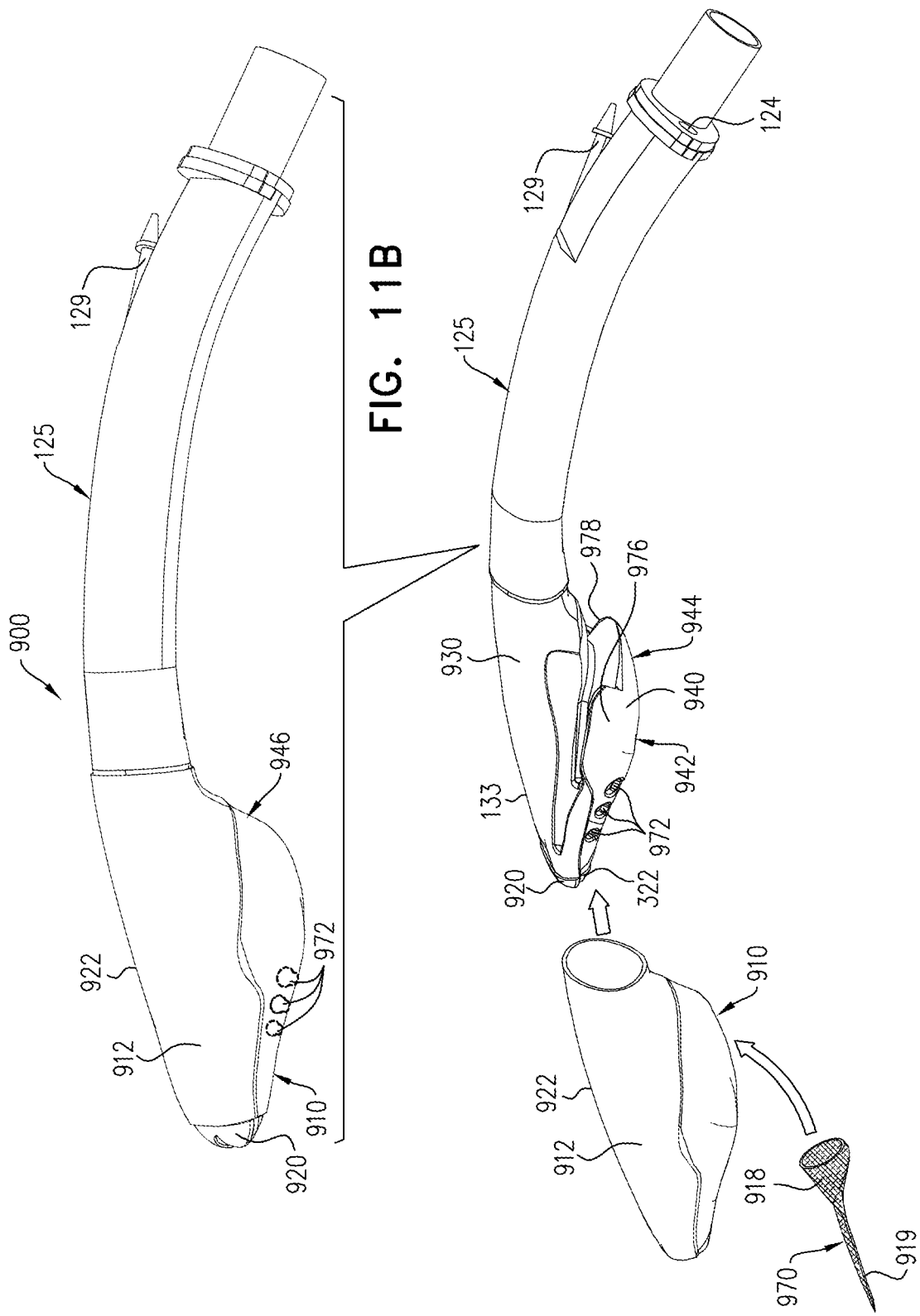

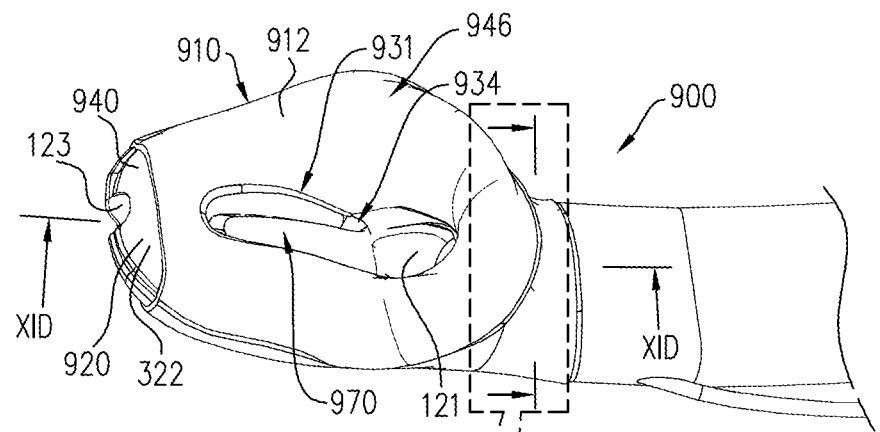
FIG. 11C
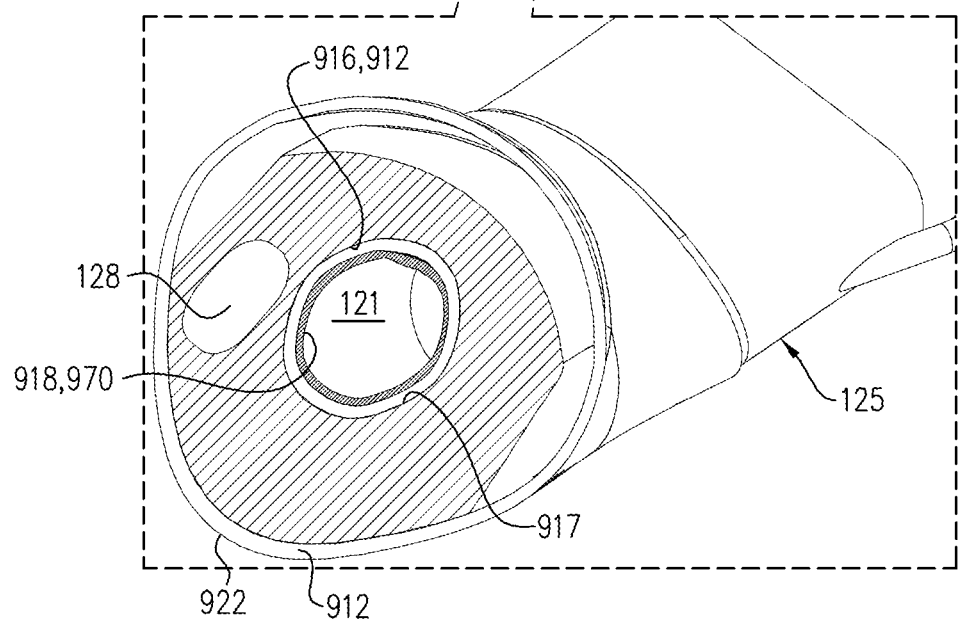

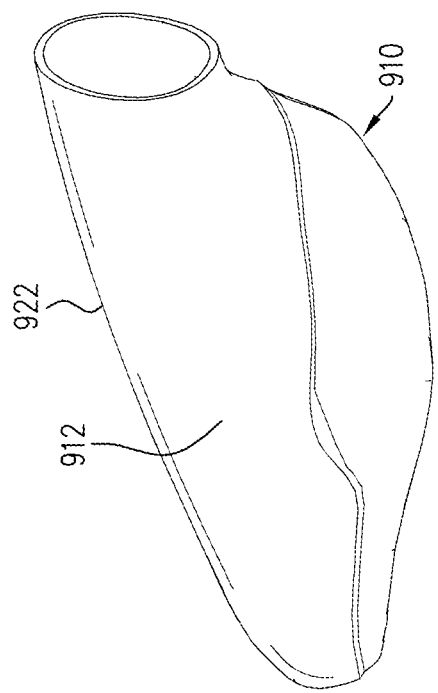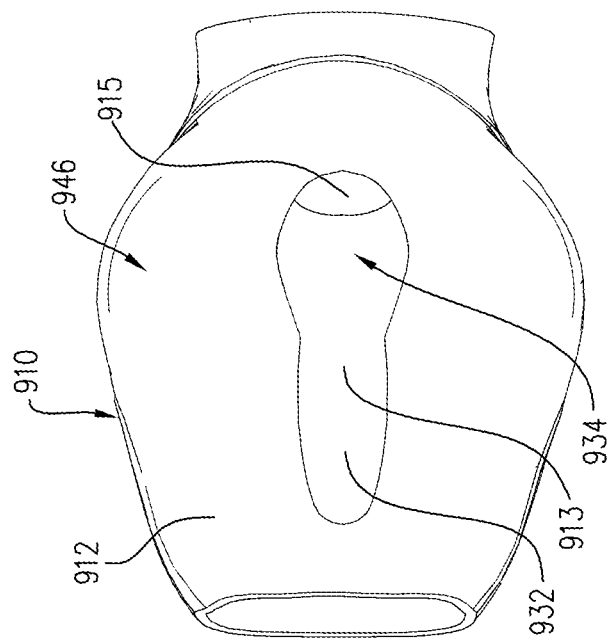

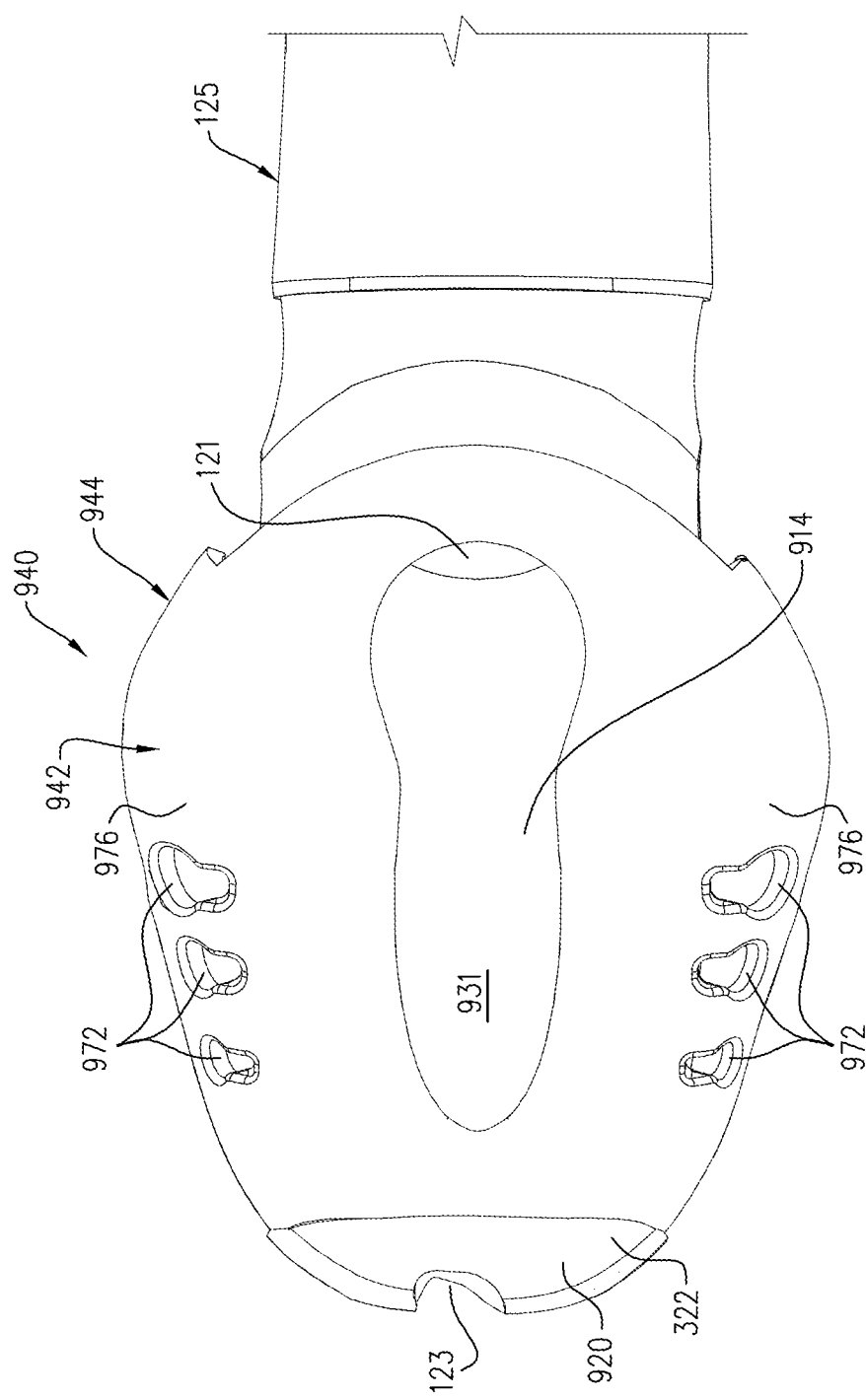

LARYNGEAL MASK CUFFS

CROSS-REFERENCE TO RELATED APPLICATIONS

The present application is a continuation of International Application PCT/IL2019/050405, filed Apr. 11, 2019, which (a) claims priority from U.S. Provisional Application 62/789,208, filed Jan. 7, 2019, and (b) claims priority from and is a continuation-in-part of International Application PCT/IL2018/051306, filed Nov. 29, 2018, which (i) claims priority from and is a continuation-in-part of U.S. application Ser. No. 15/951,564, filed Apr. 12, 2018, now U.S. Pat. No. 10,173,022, and (ii) claims priority from and is a continuation-in-part of U.S. application Ser. No. 15/878,993, filed Jan. 24, 2018, now U.S. Pat. No. 10,369,311, which claims the benefit of U.S. Provisional Application 62/592,020, filed Nov. 29, 2017. All of these applications are assigned to the assignee of the present application and are incorporated herein by reference.

FIELD OF THE APPLICATION

The present invention relates generally to lung ventilation devices, and specifically to laryngeal mask airway devices (LMA devices).

BACKGROUND OF THE APPLICATION

Laryngeal mask airway devices (LMA devices) are useful in facilitating lung ventilation by forming a low-pressure seal around the patient's laryngeal inlet, thereby avoiding the known harmful effects of endotracheal tube (ETT) devices, which form a seal within the trachea. LMA devices have become standard medical devices, instead of ETT devices, for rapidly and reliably establishing an unobstructed airway in a patient in emergency situations and in the administration of anesthetic gases. Some LMA devices further include a drainage tube, which opens into the distal tip of the mask and emerges from the mouth of the patient.

During general anesthesia, pulmonary ventilation is secured with an ETT device or by an LMA device, and attention to the risk of complications related to a high intracuff pressure is important. When the cuff-to-tracheal wall pressure exceeds the tracheal capillary pressure (130-140 cm H2O) for approximately 15 minutes, the tracheal mucous membrane becomes ischemic. The intracuff pressure approximates the cuff-to-tracheal wall pressures in high volume/low pressure cuffs, and a cuff pressure below 120 cm H2O is recommended to prevent ischemic injury. In addition, recurrent laryngeal nerve palsy has been demonstrated in up to 5% of patients after intubation, and a high cuff pressure is suspected as contributing to this complication. Similarly, in patients provided with a laryngeal mask, a high cuff pressure may lead to palsy of the lingual, hypoglossal, and recurrent laryngeal nerves, and postoperative sore throat.

The risk during anesthesia with nitrous oxide (NO) is further complicated by the fact that NO gases penetrate the cuff, thereby gradually increasing the cuff pressure above the initial setting at which the cuff was inflated.

U.S. Pat. Nos. 8,783,256, 5,632,271, and 7,305,985, all to Brain, describe laryngeal mask airway devices.

Rokamp K Z et al., in "Tracheal tube and laryngeal mask cuff pressure during anaesthesia—mandatory monitoring is in need," BMC Anesthesiology December 2010 10:20, describe "a prospective quality-control study," in which "201 patients undergoing surgery during anaesthesia (without the use of nitrous oxide) were included for determination of the cuff pressure of the tracheal tubes and laryngeal masks" (abstract).

A "Quick Reference Guide," Teleflex (Triangle Park, N.C., USA), 2013, lists various LMA Airways, having different sizes and maximum cuff volumes.

SUMMARY OF THE APPLICATION

Embodiments of the present invention provide a laryngeal mask airway (LMA) device, which comprises an inflatable annular cuff that is insertable through a mouth of a patient to an LMA-insertion location within the patient, such that an anterior side of the cuff forms a seal around a laryngeal inlet of the patient and renders the LMA device suitable for facilitating lung ventilation.

The LMA device comprises:
  a backplate, which is (a) shaped so as to define a backplate airway port, and (b) insertable through a mouth of patient;
  a non-inflatable skeleton, which extends anteriorly from the backplate, and which is shaped so as to define a skeleton anterior side that has a pre-formed shape; and
  an inflatable balloon.

The inflatable balloon is shaped so as to define an inflatable annular cuff, which (i) covers at least a portion of the skeleton anterior side, and (ii) has a cuff anterior side that is configured to form the seal around the laryngeal inlet of the patient when the inflatable annular cuff is disposed at an LMA-insertion location within a throat of the patient. For some applications, the inflatable balloon comprises an inflation port in fluid communication with an interior of the inflatable balloon. The backplate airway port is open through a cuff opening through the inflatable annular cuff.

The LMA device further comprises:
  an inflation tube having (a) a proximal end that is configured to be disposed outside the patient's mouth when the inflatable annular cuff is disposed at the LMA-insertion location, and (b) a distal end that is coupled in fluid communication with (i) an interior of the inflatable balloon (optionally, via the inflation port, if provided) for supplying air to the inflatable balloon, and (ii) at least a portion of the skeleton anterior side; and
  an airway tube having (a) a proximal end that is configured to be disposed outside the patient's mouth when the inflatable annular cuff is disposed at the LMA-insertion location, and (b) a distal end that is in fluid communication with the backplate airway port.

For some applications, the pre-formed shape of the skeleton anterior side is configured to form an anatomical fit with the laryngeal inlet of the patient when the inflatable annular cuff is disposed at the LMA-insertion location. Depending on the particular anatomy of the patient and the exact placement of the skeleton anterior side, the anatomical fit between the skeleton anterior side may form a sufficient seal with the laryngeal inlet of the patient, even without inflation of the inflatable annular cuff, in part because the cuff anterior side, even when the cuff is not inflated, improves the seal provided by the skeleton anterior side. However, if the seal is not sufficient, such as for the desired ventilation pressure, the inflatable balloon may be inflated to further improve the seal. The LMA device thus reduces installation time when an adequate seal is provided even when not inflated, by skipping the inflation step, and allows for inflation to improve the seal when necessary.

Alternatively or additionally, for some applications, the pre-formed shape of the skeleton anterior side is configured to provide a pre-inflation shape to the inflatable annular cuff when the inflatable balloon is not inflated. Providing this pre-inflation shape may prevent folding or other deformation of the inflatable annular cuff during insertion into the throat before inflation of the cuff.

For some applications, the inflatable balloon is shaped so as to define an anterior-laryngeal-chamber-region covering portion that (a) is open to the cuff opening, (b) covers a chamber-region surface defined by an anterior laryngeal chamber region into which the backplate airway port is open, and (c) is shaped so as to define a covering-portion opening in fluid communication with the cuff opening and the backplate airway port. Typically, the inflatable balloon forms an airtight seal between the covering-portion opening and the backplate airway port. For some applications, a balloon-restraining insert (a) presses the anterior-laryngeal-chamber-region covering portion of the inflatable balloon against the chamber-region surface, and (b) is disposed partially within the backplate airway port.

For some applications, the non-inflatable skeleton is shaped so as to define one or more holes between the skeleton anterior side and an interior skeleton surface of the non-inflatable skeleton, and both the skeleton anterior side and the interior skeleton surface are in fluid communication with an interior of the inflatable balloon.

For some applications, at least a portion of the non-inflatable skeleton is shaped so as to define one or more wings, which are configured to flex (e.g., laterally and/or posteriorly) with respect to the backplate when a force is applied to the wings.

There is therefore provided, in accordance with an application of the present invention, a laryngeal mask airway (LMA) device including:

a backplate, which is (a) shaped so as to define a backplate airway port, and (b) insertable through a mouth of patient;

an inflatable balloon;

an airway tube having (a) a proximal end that is configured to be disposed outside the patient's mouth when the inflatable annular cuff is disposed at the LMA-insertion location, and (b) a distal end that is in fluid communication with the backplate airway port; and a non-inflatable skeleton, which extends anteriorly from the backplate, and which is shaped so as to define a skeleton anterior side that has a pre-formed shape; and an inflation tube having (a) a proximal end that is configured to be disposed outside the patient's mouth when the inflatable annular cuff is disposed at the LMA-insertion location, and (b) a distal end that is coupled in fluid communication with (i) an interior of the inflatable balloon for supplying air to the inflatable balloon, and (ii) at least a portion of the skeleton anterior side, wherein the inflatable balloon is shaped so as to define an inflatable annular cuff, which (a) covers at least a portion of the skeleton anterior side, and (b) has a cuff anterior side that is configured to form a seal around a laryngeal inlet of the patient when the inflatable annular cuff is disposed at an LMA-insertion location within a throat of the patient, and wherein the backplate airway port is open through a cuff opening through the inflatable annular cuff.

For some applications, the non-inflatable skeleton separates and prevents at least some opposing interior portions of the inflatable annular cuff from coming into contact with one another when the inflatable balloon is deflated at a negative pressure.

For some applications, the non-inflatable skeleton is annular.

For some applications, material of the non-inflatable skeleton has a Shore hardness of between A30 and A90. For some applications, material of the inflatable annular cuff has a Shore hardness of between OO-38 and A50.

For some applications, the inflatable annular cuff has an average wall thickness of between 0.5 and 2 mm. For some applications, the inflatable annular cuff has an average wall thickness of between 0.01 and 0.3 mm.

For some applications, the non-inflatable skeleton includes a gel. For some applications, the non-inflatable skeleton further includes a coating that coats the gel.

For some applications, the non-inflatable skeleton and the backplate include different types of material from each other.

For some applications, the non-inflatable skeleton has a hardness less than a hardness of the backplate.

For some applications, the LMA cuff includes a single integral piece of material that is shaped so as to define both the non-inflatable skeleton and the backplate.

For some applications, the pre-formed shape is configured to provide a pre-inflation shape to the inflatable annular cuff when the inflatable balloon is not inflated.

For some applications, the non-inflatable skeleton includes a plurality of discrete, non-contiguous segments around an anterior side of the backplate.

For some applications, the cuff anterior side is configured to form the seal around the laryngeal inlet of the patient upon inflation of the inflatable balloon when the inflatable annular cuff is disposed at the LMA-insertion location.

For some applications, the pre-formed shape is configured to form an anatomical fit with the laryngeal inlet of the patient when the inflatable annular cuff is disposed at the LMA-insertion location.

For some applications, the non-inflatable skeleton is annular.

For some applications, the cuff anterior side is configured to form the seal around the laryngeal inlet of the patient even without inflation of the inflatable balloon, when the inflatable annular cuff is disposed at the LMA-insertion location.

For some applications, the cuff anterior side is configured such that:

the seal formed around the laryngeal inlet of the patient without inflation of the inflatable balloon provides a first level of sealing around the laryngeal inlet of the patient, and a seal formed around the laryngeal inlet of the patient upon inflation of the inflatable balloon to a pressure of 30 cm H2O when the inflatable annular cuff is disposed at the LMA-insertion location provides a second level of sealing around the laryngeal inlet of the patient, the second level greater than the first.

For some applications, an internal surface of the inflatable annular cuff and an external surface of the non-inflatable skeleton together define an inflatable chamber between the inflatable annular cuff and the non-inflatable skeleton.

For some applications, the LMA device is configured such that when the inflatable balloon is disposed in free space and inflated to a pressure of 10 cm H2O:

the internal surface of the inflatable annular cuff that helps define the inflatable chamber has an internal surface area, and the external surface of the non-inflatable skeleton that helps define the inflatable chamber has an external surface area equal to at least 25% of the internal surface area.

For some applications, the LMA device is configured such that when the inflatable balloon is disposed in free space and inflated to a pressure of 10 cm H2O, the external surface area of the external surface of the non-inflatable skeleton that helps define the inflatable chamber equals at least 40% of the internal surface area.

For some applications, the inflatable annular cuff covers an entirety of the skeleton anterior side.

For some applications:
the LMA device is shaped so as to define a gastric channel having a distal gastric opening through a distal tip portion of the non-inflatable skeleton, and
the inflatable annular cuff covers an entirety of the skeleton anterior side other than the distal gastric opening of the gastric channel.

For some applications:
the LMA device is shaped so as to define a gastric channel having a distal gastric opening through a distal tip portion of the non-inflatable skeleton, an anterior side of the distal tip portion having an area equal to less than 20% of a total area of the skeleton anterior side, and
the inflatable annular cuff covers an entirety of the skeleton anterior side other than the anterior side of the distal tip portion of the non-inflatable skeleton.

For some applications, the inflatable balloon is shaped so as to define, in addition to the inflatable annular cuff, a posterior portion that covers at least a portion of a posterior region of the backplate.

For some applications, the inflatable balloon is shaped such that respective interiors of the inflatable annular cuff and the posterior portion are in fluid communication with each other.

For some applications, the posterior portion covers an entirety of the posterior region of the backplate. For other applications, the posterior portion covers less than an entirety of the posterior region of the backplate.

For some applications:
the backplate is shaped so as to define an anterior laryngeal chamber region,
the inflatable annular cuff is shaped so as to define, around the inflatable annular cuff an annular edge that forms an airtight seal with the anterior laryngeal chamber region, and
the LMA device is configured such that when the inflatable balloon is disposed in free space and inflated to a pressure of 10 cm H2O:
the non-inflatable skeleton, along at least 25% of a length of a curved central axis of the inflatable annular cuff, reaches to within 2 mm of or intersects the curved central axis, and
the curved central axis being the set of all centroids of transverse cross-sectional sections of the inflatable annular cuff, wherein in each transverse cross-sectional section of the inflatable annular cuff around the inflatable annular cuff, one side of the inflatable annular cuff is defined by a straight line segment between (a) the annular edge and (b) a point on a surface of the posterior region closest to the annular edge.

For some applications, the LMA device is configured such that when the inflatable balloon is disposed in free space and inflated to the pressure of 10 cm H2O, the non-inflatable skeleton, along at least 50% of the length of the curved central axis of the inflatable annular cuff, reaches to within 2 mm of or intersects the curved central axis. For some applications, the LMA device is configured such that when the inflatable balloon is disposed in free space and inflated to the pressure of 10 cm H2O, the non-inflatable skeleton, along at least 75% of the length of the curved central axis of the inflatable annular cuff, reaches to within 2 mm of or intersects the curved central axis.

For some applications:
the backplate is shaped so as to define an anterior laryngeal chamber region,
the inflatable annular cuff is shaped so as to define, around the inflatable annular cuff an annular edge that forms an airtight seal with the anterior laryngeal chamber region, and
the LMA device is configured such that when the inflatable balloon is disposed in free space and inflated with air to a pressure of 10 cm H2O:
along at least 25% of a length of a curved central axis of the inflatable annular cuff, no more than 75% of a cross-sectional area of the inflatable annular cuff is filled with the air, and
the curved central axis being the set of all centroids of transverse cross-sectional sections of the inflatable annular cuff, wherein in each transverse cross-sectional section of the inflatable annular cuff around the inflatable annular cuff, one side of the inflatable annular cuff is defined by a straight line segment between (a) the annular edge and (b) a point on a surface of the posterior region closest to the annular edge.

For some applications, the LMA device is configured such that when the inflatable balloon is disposed in free space and inflated with the air to the pressure of 10 cm H2O, along at least 50% of the length of the curved central axis of the inflatable annular cuff, no more than 75% of the cross-sectional area of the inflatable annular cuff is filled with the air. For some applications, the LMA device is configured such that when the inflatable balloon is disposed in free space and inflated with the air to the pressure of 10 cm H2O, along at least 75% of the length of the curved central axis of the inflatable annular cuff, no more than 75% of the cross-sectional area of the inflatable annular cuff is filled with the air.

For some applications, the LMA device is configured such that when the inflatable balloon is disposed in free space and inflated with the air to the pressure of 10 cm H2O, along at least 25% of the length of the curved central axis of the inflatable annular cuff, no more than 50% of the cross-sectional area of the inflatable annular cuff is filled with the air.

For some applications, the inflatable balloon is shaped so as to define only the inflatable annular cuff.

For some applications:
the backplate is shaped so as to define an anterior laryngeal chamber region into which the backplate airway port is open, and
the inflatable balloon is shaped so as to define an anterior-laryngeal-chamber-region covering portion that (a) is open to the cuff opening, (b) covers a chamber-region surface defined by the anterior laryngeal chamber region, and (c) is shaped so as to define a covering-portion opening in fluid communication with the cuff opening and the backplate airway port.

For some applications, the inflatable balloon forms an airtight seal between the covering-portion opening and the backplate airway port.

For some applications, the apparatus further includes a balloon-restraining insert, which (a) presses the anterior-laryngeal-chamber-region covering portion of the inflatable balloon against the chamber-region surface, and (b) is disposed partially within the backplate airway port. For some applications, the balloon-restraining insert is shaped so as to define a tab that is in contact with a portion of the anterior-laryngeal-chamber-region covering portion so as to press the anterior-laryngeal-chamber-region covering portion against the chamber-region surface.

For some applications:
the inflatable balloon is shaped so as to define a balloon tubular portion, and
the balloon-restraining insert presses the balloon tubular portion against an internal surface of the backplate airway port, such that the inflatable balloon forms the airtight seal between the covering-portion opening and the backplate airway port.

For some applications, the balloon-restraining insert is shaped so as to define an insert tubular portion, which presses the balloon tubular portion against the internal surface of the backplate airway port.

For some applications, the inflatable balloon is shaped so as to define, in addition to the inflatable annular cuff and the anterior-laryngeal-chamber-region covering portion, a posterior portion that covers at least a portion of a posterior region of the backplate. For some applications, the posterior portion covers an entirety of the posterior region of the backplate.

For some applications:
the non-inflatable skeleton is shaped so as to define one or more holes between the skeleton anterior side and an interior skeleton surface of the non-inflatable skeleton, and
both the skeleton anterior side and the interior skeleton surface are in fluid communication with an interior of the inflatable balloon.

For some applications, at least a portion of the non-inflatable skeleton is shaped so as to define one or more wings, which are configured to flex with respect to the backplate when a force is applied to the wings. For some applications, the one or more wings are configured to laterally flex with respect to the backplate when a lateral force is applied to the wings. For some applications, a proximal portion of the one or more wings is configured to posteriorly flex with respect to the backplate when a posteriorly-directed force is applied to the wings. For some applications, the one or more wings are shaped so as to define an interior skeleton surface of the non-inflatable skeleton, the non-inflatable skeleton is shaped so as to define one or more holes between the skeleton anterior side and the interior skeleton surface of the non-inflatable skeleton, and both the skeleton anterior side and the interior skeleton surface are in fluid communication with an interior of the inflatable balloon.

For some applications, the non-inflatable skeleton and the backplate include two non-integral pieces attached together.

For some applications, the non-inflatable skeleton is attached to a portion of a backplate surface of the backplate at a cuff-backplate interface surface, and the inflatable annular cuff and the cuff-backplate interface surface together enclose an entirety of the non-inflatable skeleton.

For some applications:
the LMA device is shaped so as to define a gastric channel having a distal gastric opening through a distal tip portion of the non-inflatable skeleton, an anterior side of the distal tip portion having an area equal to less than 20% of a total area of the skeleton anterior side, and
the non-inflatable skeleton is attached to a portion of a backplate surface of the backplate at a cuff-backplate interface surface, and the inflatable annular cuff and the cuff-backplate interface surface together enclose an entirety of the non-inflatable skeleton other than the anterior side of the distal tip portion of the non-inflatable skeleton.

For some applications:
the LMA device is shaped so as to define a gastric channel having a distal gastric opening through a distal tip portion of the non-inflatable skeleton, and the non-inflatable skeleton is attached to a portion of a backplate surface of the backplate at a cuff-backplate interface surface, and the inflatable annular cuff and the cuff-backplate interface surface together enclose an entirety of the non-inflatable skeleton other than the distal gastric opening of the gastric channel.

For some applications:
the backplate is shaped so as to define an anterior laryngeal chamber region and a posterior region on the other, posterior side of backplate,
the inflatable annular cuff is shaped so as to define, around the inflatable annular cuff (a) a first annular edge that forms an airtight seal with the anterior laryngeal chamber region, and (b) a second annular edge that forms an airtight seal with the posterior region, and
the LMA device is configured such that when the inflatable balloon is disposed in free space and inflated to a pressure of 10 cm H2O:
the non-inflatable skeleton, along at least 25% of a length of a curved central axis of the inflatable annular cuff, reaches to within 2 mm of or intersects the curved central axis, and
the curved central axis being the set of all centroids of transverse cross-sectional sections of the inflatable annular cuff, wherein in each transverse cross-sectional section of the inflatable annular cuff around the inflatable annular cuff, one side of the inflatable annular cuff is defined by a straight line segment between the first annular edge and the second annular edge.

For some applications, the LMA device is configured such that when the inflatable balloon is disposed in free space and inflated to the pressure of 10 cm H2O, the non-inflatable skeleton, along at least 50% of the length of the curved central axis of the inflatable annular cuff, reaches to within 2 mm of or intersects the curved central axis. For some applications, the LMA device is configured such that when the inflatable balloon is disposed in free space and inflated to the pressure of 10 cm H2O, the non-inflatable skeleton, along at least 75% of the length of the curved central axis of the inflatable annular cuff, reaches to within 2 mm of or intersects the curved central axis.

For some applications:
the backplate is shaped so as to define an anterior laryngeal chamber region and a posterior region on the other, posterior side of backplate,
the inflatable annular cuff is shaped so as to define, around the inflatable annular cuff (a) a first annular edge that forms an airtight seal with the anterior laryngeal chamber region, and (b) a second annular edge that forms an airtight seal with the posterior region, and
the LMA device is configured such that when the inflatable balloon is disposed in free space and inflated with air to a pressure of 10 cm H2O:
along at least 25% of a length of a curved central axis of the inflatable annular cuff, no more than 75% of a cross-sectional area of the inflatable annular cuff is filled with the air, and
the curved central axis being the set of all centroids of transverse cross-sectional sections of the inflatable annular cuff, wherein in each transverse cross-sectional section of the inflatable annular cuff around the inflatable annular cuff, one side of the inflatable annular cuff is defined by a straight line segment between the first annular edge and the second annular edge.

For some applications, the LMA device is configured such that when the inflatable balloon is disposed in free space and inflated with the air to the pressure of 10 cm H2O, along at least 50% of the length of the curved central axis of the inflatable annular cuff, no more than 75% of the cross-sectional area of the inflatable annular cuff is filled with the air. For some applications, the LMA device is configured such that when the inflatable balloon is disposed in free space and inflated with the air to the pressure of 10 cm H2O, along at least 75% of the length of the curved central axis of the inflatable annular cuff, no more than 75% of the cross-sectional area of the inflatable annular cuff is filled with the air.

For some applications, the LMA device is configured such that when the inflatable balloon is disposed in free space and inflated with the air to the pressure of 10 cm H2O, along at least 25% of the length of the curved central axis of the inflatable annular cuff, no more than 50% of the cross-sectional area of the inflatable annular cuff is filled with the air.

For some applications:

the inflatable balloon, when disposed in free space, is characterized by a pressure-volume curve that represents the pressure in the inflatable balloon when inflated, from a deflated negative pressure, by different volumes of ambient-pressure air, which include a low-pressure volume that results in a low pressure of 10 cm H2O, and the pressure-volume curve includes:

a low-pressure-range average rate of change over a low-pressure volume interval between 1.0 and 1.2 times the low-pressure volume, a medium-pressure-range average rate of change over a medium-pressure volume interval between 2.0 and 2.2 times the low-pressure volume, and a medium pressure at a medium volume of the inflatable balloon equal to 2.0 times the low-pressure volume, the medium-pressure-range average rate of change is less than 0.5 times the low-pressure-range average rate of change, and the medium pressure is between 20 and 200 cm H2O.

For some applications, the medium pressure is between 20 and 120 cm H2O. For some applications, the medium pressure is between 20 and 70 cm H2O. For some applications, the medium pressure is between 20 and 40 cm H2O.

For some applications, the medium-pressure-range average rate of change is equal to less than 0.4 times the low-pressure-range average rate of change.

There is further provided, in accordance with an application of the present invention, a method including:

inserting a backplate, a non-inflatable skeleton, and an inflatable balloon of a laryngeal mask airway (LMA) device through a mouth of a patient and disposing, at an LMA-insertion location within a throat of the patient, an inflatable annular cuff defined by the inflatable balloon, such that (a) a proximal end of an inflation tube is disposed outside the patient's mouth and (b) a proximal end of an airway tube of the LMA device is disposed outside the patient's mouth; and ventilating lungs of the patient using the LMA device, wherein the non-inflatable skeleton extends anteriorly from the backplate, and is shaped so as to define a skeleton anterior side that has a pre-formed shape, wherein a distal end of the inflation tube is coupled in fluid communication with (i) an interior of the inflatable balloon for supplying air to the inflatable balloon, and (ii) at least a portion of the skeleton anterior side, wherein a distal end of the airway tube is in fluid communication with a backplate airway port defined by the backplate, wherein the backplate airway port is open through a cuff opening through the inflatable annular cuff, wherein the inflatable annular cuff covers at least a portion of the skeleton anterior side, and wherein the inflatable annular cuff has a cuff anterior side that is configured to form a seal around a laryngeal inlet of the patient when the inflatable annular cuff is disposed at the LMA-insertion location within the throat of the patient.

For some applications, the non-inflatable skeleton separates and prevents at least some opposing interior portions of the inflatable annular cuff from coming into contact with one another when the inflatable balloon is deflated at a negative pressure.

For some applications:

the pre-formed shape is configured to provide a pre-inflation shape to the inflatable annular cuff when the inflatable balloon is not inflated, and the method further includes inflating the inflatable balloon such that the cuff anterior side forms the seal around the laryngeal inlet of the patient.

For some applications:

the cuff anterior side is configured to form the seal around the laryngeal inlet of the patient upon inflation of the inflatable balloon when the inflatable annular cuff is disposed at the LMA-insertion location, and the method further includes inflating the inflatable balloon such that the cuff anterior side forms the seal around the laryngeal inlet of the patient.

For some applications, the pre-formed shape is configured to form an anatomical fit with the laryngeal inlet of the patient when the inflatable annular cuff is disposed at the LMA-insertion location.

For some applications, the cuff anterior side is configured to form the seal around the laryngeal inlet of the patient even without inflation of the inflatable balloon, when the inflatable annular cuff is disposed at the LMA-insertion location.

For some applications:

the cuff anterior side is configured such that the seal formed around the laryngeal inlet of the patient without inflation of the inflatable balloon provides a first level of sealing around the laryngeal inlet of the patient, and the method further includes inflating the inflatable balloon such that the seal formed around the laryngeal inlet of the patient provides a second level of sealing around the laryngeal inlet of the patient, the second level greater than the first.

For some applications:

inserting includes inserting the backplate, the non-inflatable skeleton, and the inflatable balloon without inflating the inflatable balloon, ventilating the lungs includes applying a first level of ventilation while the inflatable balloon is not inflated and the seal formed around the laryngeal inlet of the patient thus provides the first level of sealing around the laryngeal inlet of the patient, inflating the inflatable balloon includes inflating the inflatable balloon after beginning applying the first level of ventilation, and the method further includes, after inflating the inflatable balloon, applying a second level of ventilation that is greater than the first level of ventilation and thus requires the greater second level of sealing around the laryngeal inlet of the patient.

For some applications:

the cuff anterior side is configured such that the seal formed around the laryngeal inlet of the patient without inflation of the inflatable balloon provides a first level of sealing around the laryngeal inlet of the patient, inserting includes inserting the backplate, the non-inflatable skeleton, and the inflatable balloon without inflating the inflatable balloon, ventilating the lungs includes applying a desired level of ventilation while the inflatable balloon is not inflated and the seal formed around the laryngeal inlet of the patient thus provides the first level of sealing around the laryngeal inlet of the patient, and the method further includes:

after beginning ventilating the lungs, ascertaining whether the first level of sealing is sufficient for the desired level of ventilation; and upon ascertaining the first level of sealing is not sufficient for the desired level of ventilation, inflating the inflatable balloon such that the cuff anterior side the seal formed around the laryngeal inlet of the patient provides a second level of sealing around the laryngeal inlet of the patient, the second level greater than the first and sufficient for the desired level of ventilation.

The present invention will be more fully understood from the following detailed description of embodiments thereof, taken together with the drawings, in which:

BRIEF DESCRIPTION OF THE DRAWINGS

FIGS. 2A-D are schematic illustrations of respective views of the LMA device of FIG. 1 with an inflatable annular cuff thereof inflated at a low pressure, in accordance with an application of the present invention;

FIGS. 3A-D are schematic illustrations of respective views of the LMA device of FIG. 1 with the inflatable annular cuff thereof inflated at a working medium pressure, in accordance with an application of the present invention;

FIGS. 4A-D are schematic illustrations of respective views of another LMA device with an inflatable annular cuff inflated at a low pressure, in accordance with an application of the present invention;

FIGS. 5A-D are schematic illustrations of respective views of yet another LMA device with an inflatable annular cuff inflated at a low pressure, in accordance with an application of the present invention;

FIGS. 6A-D are schematic illustrations of respective views of the LMA device of FIGS. 5A-D with the inflatable annular cuff thereof inflated at a working medium pressure, in accordance with an application of the present invention;

FIGS. 7A-D are schematic illustrations of respective views of still another LMA device with an inflatable annular cuff inflated at a working medium pressure, in accordance with an application of the present invention;

FIGS. 11A-D are schematic illustrations of respective views of yet another LMA device, in accordance with an application of the present invention;

FIGS. 12A-C are schematic illustrations of several views of an inflatable balloon of the LMA device of FIGS. 11A-D, in accordance with an application of the present invention;

FIGS. 13A-B are schematic illustrations of two views of a non-inflatable skeleton and a portion of an airway tube of the LMA device of FIGS. 11A-D, in accordance with an application of the present invention;

DETAILED DESCRIPTION OF APPLICATIONS

Figure 1:
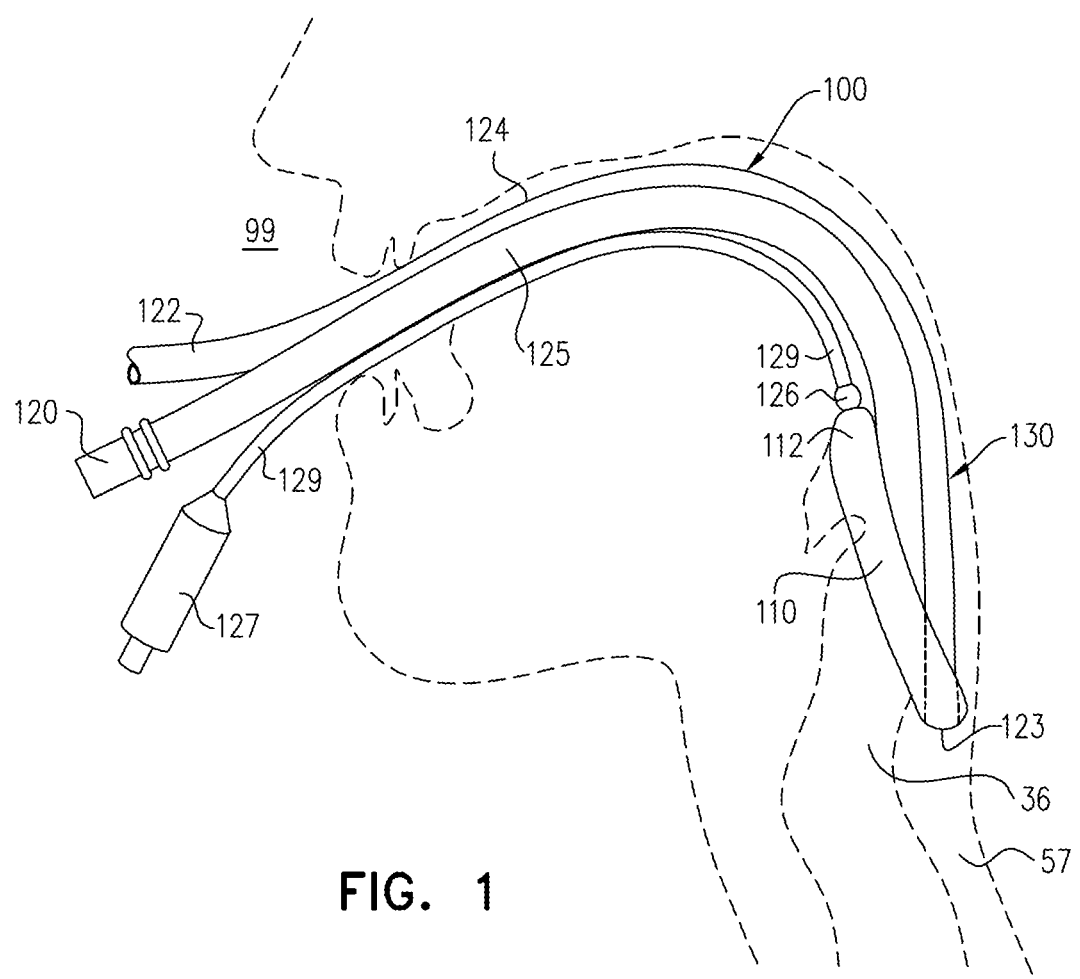
FIG. 1 is a schematic illustration of a laryngeal mask airway (LMA) device, in accordance with an application of the present invention.

FIG. 1 is a schematic illustration of a laryngeal mask airway (LMA) device 100, in accordance with an application of the present invention. In typical use, LMA device 100 is inserted into the throat while deflated (the upper surface of the throat is bounded by hard and soft palates). LMA device 100 is lodged in the pharynx at the base of the hypopharynx where the throat divides into the trachea 36 and the esophagus 57. For some applications, after LMA device 100 is thus lodged in the pharynx, an inflatable annular cuff 110 defined by an inflatable balloon 112 of LMA device 100 is inflated at the LMA-insertion location with the patient, as illustrated in FIG. 1.

Reference is still made to FIG. 1 and is additionally made to FIGS. 2A-D and 3A-D, which are schematic illustrations of respective views of LMA device 100 with inflatable annular cuff 110 inflated at a low pressure and a working medium pressure $P_M$, respectively, in accordance with an application of the present invention. FIGS. 2A, 2B, and 2C are anterior, side, and posterior views of LMA device 100, respectively, and FIGS. 3A, 3B, and 3C are anterior, side, and posterior views of LMA device 100, respectively. FIGS. 2D and 3D are cross-sectional views take along lines IID-IID of FIG. 2C and IIID-IIID of FIG. 3C, respectively. FIG. 3D also shows in phantom inflatable annular cuff 110 inflated at the low pressure shown in FIG. 2D. For example, the low pressure may be 10 cm H2O, and/or the working medium pressure $P_M$ may be between 20 and 200 cm H2O, such as between 20 and 120 cm H2O, e.g., between 20 and 70 cm H2O, such as between 20 and 40 cm H2O. It is noted that, for clarity of illustration, inflatable annular cuff 110 (as well as the other inflatable annular cuffs illustrated in the figures) is shown as translucent. In practice, the cuffs may be translucent, transparent, or opaque, as is known in the art.

As is conventional in the LMA cuff art, inflatable annular cuff 110 is a single-layer cuff, i.e., has only a single wall, as can be seen in the cross-sectional figures. The wall thicknesses of inflatable annular cuff 110 described, as well as the wall thicknesses of the prior art cuffs described hereinbelow with reference to these figures, relate to the thickness of this single layer, i.e., single wall. The present invention does not relate to multi-layer cuffs.

For some applications, inflatable annular cuff 110 comprises a highly elastic material, such as described hereinbelow with reference to FIGS. 16A-B. For other applications, inflatable annular cuff 110 comprises a material having minimal elasticity as commonly used in medical device cuff technology, e.g., PVC or polyurethane.

Typically, inflatable annular cuff 110, when disposed in free space and inflated, has an asymmetric toroidal tubular shape, generated, for example, by an asymmetrical oval or ellipse having a wider proximal 20% region and narrower distal 20% region.

For some applications, the wall of inflatable annular cuff 110 is configured to have an air permeability such that inflatable annular cuff 110 leaks less than 1 cc of air during an eight-hour period immediately following inflation of inflatable annular cuff 110 with air to a pressure of 30 cm H2O, when disposed in free space. As used in the present application, including in the claims, "disposed in free space" means disposed in ambient air 99 at atmospheric pressure at 20 degrees Celsius without being constrained by the patient's anatomy, a delivery tool, or anything else.

LMA device comprises an airway tube 125, which is installed through the mouth of the patient. Airway tube 125 has a proximal end 120 that is configured to be disposed outside the patient's mouth when the cuff is at the LMA-insertion location. Proximal end 120 typically defines an airway connector port, which is configured for connection to air or other ventilating apparatus for the patient's lungs.

LMA device 100 further comprises a backplate 130 having a backplate airway port 121 (shown in FIGS. 2A and 3A) through which airway tube 125 can establish a free externally accessible ventilation passage, via the patient's mouth and throat, and past the epiglottis to the larynx. Airway tube 125 has a distal end that is in fluid communication with backplate airway port 121. Backplate airway port 121 is open through a cuff opening 134 through inflatable annular cuff 110, i.e., through the central open space surrounded by the annulus of inflatable annular cuff 110. For example, backplate 130 may comprise an elastomer such as silicone rubber, PVC, or polyurethane, which may be the same material as or a different material from inflatable balloon 112 and/or non-inflatable skeleton 140, as described hereinbelow, and may be relatively stiff due to its thickness of more than 1 mm. Backplate 130 typically has a one-piece, integral spoon-shape having an oval portion. Opposite sides of the oval portion are typically defined by a convex pharyngeal side and a concave laryngeal side. The periphery of the oval portion is hermetically bonded to the periphery of inflatable annular cuff 110, so as to establish, when placed within the human patient, separation between an anterior laryngeal chamber region 131 and a posterior (pharyngeal) region 133 on the other side of backplate 130.

Inflatable annular cuff 110 is insertable through a mouth of a patient to an LMA-insertion location within the patient, typically when the cuff is deflated. Backplate 130 is attached to inflatable annular cuff 110.

In some applications of the present invention, such as shown in FIGS. 1, 2A-D, and 3A-D, LMA device 100 is of the gastro-laryngeal mask (GLM) type, in which a drainage tube 124 (a) extends from a gastric channel 128 (labeled in FIGS. 2D and 3D) having a distal gastric opening 123 (labeled in FIGS. 1, 2A, and 3A) at a location near a distal end of inflatable annular cuff 110, and (b) has a proximal drainage port 122 at location outside the patient's mouth when inflatable annular cuff 110 is at the LMA-insertion location. Drainage tube 124 enables extraction and external removal of gastric-discharge products from esophagus 57. Drainage tube 124 follows the general course of airway tube 125. Such GLM devices are commonly used in hospital settings in which evacuation suction sources are available, while simpler configurations of LMA devices without evacuation tubes are more commonly used in emergency intubations settings. Although the figures show drainage tube 124, drainage tube 124 is not an essential element of LMA device 100, and is not provided in some embodiments of the invention. Therefore, unless specifically stated to the contrary, all features of LMA device 100 described herein apply to LMA designs both with and without drainage tube 124.

LMA device 100 further comprises an externally-accessible inflation tube 129 and an inflation port 126 on inflatable annular cuff 110 for supplying air to the cuff and extracting air from (and therefore collapsing) the inflatable balloon 112, for inserting the cuff into and removing the cuff from the patient. A distal end of inflation tube 129 is coupled in fluid communication with an interior of inflatable balloon 112, typically via inflation port 126. Typically, an inflation check-valve 127 is disposed in inflation tube 129 for holding a given inflation of inflatable annular cuff 110. For some applications, inflation tube 129 comprises an inflation tube proximal port connector that comprises a male conical fitting with a taper. For some applications, the taper is at least a 5% taper. For some applications, the taper is a 6% taper, and the male conical fitting with the 6% taper complies with International Standard ISO 594-1:1986, which is the standard for connections to conventional inflation lumen proximal ports of LMA masks. Typically, though not necessarily, before inflatable annular cuff 110 is inserted to the patient, an inflation/deflation device is actuated to apply a vacuum, via inflation tube 129, to the interior of inflatable annular cuff 110 sufficient to fully deflate the cuff prior to insertion of the cuff through the mouth of the patient. For concreteness of discussion and test procedures, initial inflation volumes are assumed to start from a deflated state in which the cuff is deflated at suction pressure of negative 30 cm H2O (−30 cm H2O).

LMA device 100 further comprises a non-inflatable skeleton 140, which extends anteriorly from backplate 130, and which is shaped so as to define a skeleton anterior side 142 that has a pre-formed shape 144. Inflatable annular cuff 110 covers at least a portion of skeleton anterior side 142. Inflatable annular cuff 110 has a cuff anterior side 146 that is configured to form a seal around a laryngeal inlet of the patient when inflatable annular cuff 110 is disposed at an LMA-insertion location within a throat of the patient. Skeleton anterior side 142 and cuff anterior side 146 face at least partially anteriorly and typically also face at least partially anteriorly-laterally. The distal end of inflation tube 129 is coupled in fluid communication with at least a portion of skeleton anterior side 142.

For some applications, such as shown in FIGS. 2A, 2C, 3A, and 3C, non-inflatable skeleton 140 is annular.

For some applications, cuff anterior side 146 is configured to form the seal around the laryngeal inlet of the patient upon inflation of inflatable balloon 112 when inflatable annular cuff 110 is disposed at the LMA-insertion location.

For some applications, pre-formed shape 144 is configured to form an anatomical fit with the laryngeal inlet of the patient when inflatable annular cuff 110 is disposed at the LMA-insertion location. For some of these applications, cuff anterior side 146 is configured to form the seal around the laryngeal inlet of the patient upon inflation of inflatable balloon 112 when inflatable annular cuff 110 is disposed at the LMA-insertion location.

Alternatively, for some of these applications, cuff anterior side 146 is configured to form the seal around the laryngeal inlet of the patient even without inflation of inflatable balloon 112, when inflatable annular cuff 110 is disposed at the LMA-insertion location. For some of these applications, cuff anterior side 146 is configured such that (a) the seal formed around the laryngeal inlet of the patient without inflation of inflatable balloon 112 provides a first level of sealing around the laryngeal inlet of the patient, and (b) a seal formed around the laryngeal inlet of the patient upon inflation of inflatable balloon 112 (e.g., to a pressure of 30 cm H2O) when inflatable annular cuff 110 is disposed at the LMA-insertion location provides a second level of sealing around the laryngeal inlet of the patient, the second level greater than the first, such as described hereinbelow. The second level of sealing may (a) seal at higher ventilation air pressures provided through airway tube 125, or (b) result in less air leakage at the same ventilation air pressures provided through airway tube 125. For some applications, the first level of sealing is measured as the percentage of air leakage under a standard ventilation setting in continuous mandatory ventilation (CMV) volume-control mode with a respiratory rate of 12 cycles/minute, a tidal volume of 400 cc and PEEP of 5 cm H2O, to a human patient.

Alternatively or additionally, for some applications, preformed shape 144 is configured to provide a pre-inflation shape to inflatable annular cuff 110 when inflatable balloon 112 is not inflated. Providing this pre-inflation shape may prevent folding or other deformation of inflatable annular cuff 110 during insertion into the throat before inflation of the cuff.

Typically, an internal surface 150 of inflatable annular cuff 110 and an external surface 152 of non-inflatable skeleton 140 together define an inflatable chamber 154 between inflatable annular cuff 110 and non-inflatable skeleton 140. External surface 152 of non-inflatable skeleton 140 typically includes skeleton anterior side 142.

For some applications, LMA device 100 is configured such that when inflatable balloon 112 is disposed in free space and inflated to a pressure of 10 cm H2O, such as shown in FIGS. 2A-D: (a) internal surface 150 of inflatable annular cuff 110 that helps define inflatable chamber 154 has an internal surface area, and (b) external surface 152 of non-inflatable skeleton 140 that helps define inflatable chamber 154 has an external surface area equal to at least 25% of the internal surface area, e.g., at least 40%, such as at least 60%, of the internal surface area.

For some applications in which LMA device 100 is shaped so as to define the above-mentioned gastric channel 128, inflatable annular cuff 110 covers an entirety of skeleton anterior side 142 other than distal gastric opening 123 of gastric channel 128, such as shown in FIGS. 2A-D and 3A-D. (Inflatable annular cuff 110 optionally covers additional portions of non-inflatable skeleton 140, such as lateral surfaces thereof, and/or a portion of backplate 130.)

For some applications, non-inflatable skeleton 140 and backplate 130 comprise different types of material from each other, such as shown in FIGS. 2A-D and 3A-D. For some of these applications, non-inflatable skeleton 140 has a hardness less than a hardness of backplate 130.

Alternatively or additionally, for some applications, non-inflatable skeleton 140 and backplate 130 comprise two non-integral pieces attached together, such as shown in FIGS. 2A-D and 3A-D. For some of these applications in which LMA device 100 is shaped so as to define the above-mentioned gastric channel 128, non-inflatable skeleton 140 is attached to a portion of a backplate surface of backplate 130 at a cuff-backplate interface surface 156, and inflatable annular cuff 110 and cuff-backplate interface surface 156 together enclose an entirety of non-inflatable skeleton 140 other than distal gastric opening 123 of gastric channel 128. (Inflatable annular cuff 110 optionally covers additional portions of non-inflatable skeleton 140, such as lateral surfaces thereof, and/or a portion of backplate 130.)

For some applications, non-inflatable skeleton 140 separates and prevents at least some opposing interior portions of inflatable annular cuff 110 from coming into contact with one another when inflatable annular cuff 110 is deflated at a negative pressure (e.g., at suction pressure of negative 30 cm H2O (−30 cm H2O)). This feature may be considered another manifestation of the possible dispositions of non-inflatable skeleton 140 with respect to inflatable annular cuff 110 described hereinabove.

As mentioned above, typically, though not necessarily, before inflatable annular cuff 110 is inserted to the patient, an inflation/deflation device is actuated to apply a vacuum, via inflation tube 129, to the interior of inflatable annular cuff 110 sufficient to fully deflate the cuff prior to insertion of the cuff through the mouth of the patient. For applications in which non-inflatable skeleton 140 separates and prevents at least some opposing interior portions of inflatable annular cuff 110 from coming into contact with one another when inflatable annular cuff 110 is deflated at a negative pressure, non-inflatable skeleton 140 prevents inflatable annular cuff 110 from fully collapsing and losing its shape when deflated. By contrast, upon deflation before insertion, conventional LMA cuffs tend to fold, which may interfere with the proper anatomical placement of the LMA cuffs.

For some applications, non-inflatable skeleton 140 comprises a gel. Optionally, non-inflatable skeleton 140 further comprises a coating that coats the gel, such as a membrane. Alternatively, for some applications, non-inflatable skeleton 140 comprises a polymer, such as polyvinyl chloride (PVC).

For some applications, material of non-inflatable skeleton 140 has a Shore hardness of between A30 and A90, such as between A50 and A90, e.g., between A60 and A80, such as A70. Alternatively or additionally, for some applications, material of inflatable annular cuff 110 has a Shore hardness of between OO-38 and A50, such as between A0 and A30, e.g., between A5 and A20.

For some applications, inflatable annular cuff 110 has an average wall thickness of between 0.5 and 2 mm or between 0.01 and 0.3 mm.

Reference is now made to FIGS. 4A-D, which are schematic illustrations of respective views of an LMA device 300 with an inflatable annular cuff 310 inflated at a low pressure, in accordance with an application of the present invention. FIGS. 4A, 4B, and 4C are anterior, side, and posterior views of LMA device 300, respectively, and FIG. 4D is a cross-sectional view take along lines IVD-IVD of FIG. 4C. For example, the low pressure may be 10 cm H2O. Other than as described below, LMA device 300 is identical to LMA device 100, described hereinabove with reference to FIGS. 1-3D, and like reference numerals refer to like elements. LMA device 300 comprises an inflatable balloon 312 that is shaped so as to define inflatable annular cuff 310. The features of LMA device 300 may also be implemented in combination with the other LMA devices described herein, mutatis mutandis.

LMA device 300 is shaped so as to define gastric channel 128 having distal gastric opening 123 through a distal tip portion 320 of non-inflatable skeleton 140. An anterior side 322 of distal tip portion 320 has an area equal to less than 20% of a total area of skeleton anterior side 142.

For some applications, inflatable annular cuff 110 covers an entirety of skeleton anterior side 142 other than anterior side 322 of distal tip portion 320 of non-inflatable skeleton 140.

For some applications, non-inflatable skeleton 140 is attached to a portion of a backplate surface of backplate 130 at cuff-backplate interface surface 156, and inflatable annular cuff 110 and cuff-backplate interface surface 156 together enclose an entirety of non-inflatable skeleton 140 other than anterior side 322 of distal tip portion 320 of non-inflatable skeleton 140.

Reference is now made to FIGS. 5A-D and 6A-D, which are schematic illustrations of respective views of an LMA device 400 with an inflatable annular cuff 410 inflated at a low pressure and a working medium pressure $P_M$, respectively, in accordance with an application of the present invention. FIGS. 5A, 5B, and 5C are anterior, side, and posterior views of LMA device 400, respectively, and FIGS. 6A, 6B, and 6C are anterior, side, and posterior views of LMA device 400, respectively. FIGS. 5D and 6D are cross-sectional views take along lines VD-VD of FIG. 5C and VID-VID of FIG. 6C, respectively. FIG. 6D also shows in phantom inflatable annular cuff 410 inflated at the low pressure shown in FIG. 5D. For example, the low pressure may be 10 cm H2O, and/or the working medium pressure $P_M$ may be between 20 and 200 cm H2O, such as between 20 and 120 cm H2O, e.g., between 20 and 70 cm H2O, such as between 20 and 40 cm H2O. LMA device 400 comprises an inflatable balloon 412 that is shaped so as to define inflatable annular cuff 410. Other than as described below, LMA device 400 is identical to LMA device 100, described hereinabove with reference to FIGS. 1-3D, and like reference numerals refer to like elements. The features of LMA device 400 may also be implemented in combination with the other LMA devices described herein, mutatis mutandis.

In this configuration, inflatable balloon 412 is shaped so as to define, in addition to inflatable annular cuff 410, a posterior portion 422 that covers at least a portion of a posterior region 133 of backplate 130, such as at least 75% of an area of posterior region 133, e.g., the entire posterior region 133. Typically, inflatable balloon 412 is shaped such that respective interiors of inflatable annular cuff 410 and posterior portion 422 are in fluid communication with each other. (Backplate airway port 121 is open through a cuff opening 434 through inflatable annular cuff 410, i.e., through the central open space surrounded by the annulus of inflatable annular cuff 410.)

(By way of contrast, in the configurations shown in FIGS. 1-4D and 8-10, the inflatable balloon may be shaped so as to define only the inflatable annular cuff.)

Reference is now made to FIGS. 7A-D, which are schematic illustrations of respective views of an LMA device 500 with an inflatable annular cuff 510 inflated at a working medium pressure $P_M$, in accordance with an application of the present invention. FIGS. 7A, 7B, and 7C are anterior, side, and posterior views of LMA device 500, respectively, and FIG. 7D is a cross-sectional view take along lines VIIID-VIIID of FIG. 7C. FIG. 7D also shows in phantom inflatable annular cuff 510 inflated at a low pressure. For example, the low pressure may be 10 cm H2O, and/or the working medium pressure $P_M$ may be between 20 and 200 cm H2O, such as between 20 and 120 cm H2O, e.g., between 20 and 70 cm H2O, such as between 20 and 40 cm H2O. LMA device 500 comprises an inflatable balloon 512 that is shaped so as to define inflatable annular cuff 510.

LMA device 500 implements the features of LMA device 300, described hereinabove with reference to FIGS. 4A-D in combination with the features of LMA device 400, described hereinabove with reference to FIGS. 5A-D and 6A-D, and like reference numerals refer to like elements. The features of LMA device 500 may also be implemented in combination with the other LMA devices described herein, mutatis mutandis.

Figure 8:
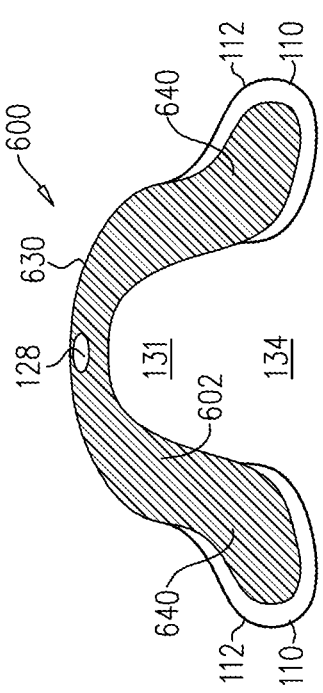
FIG. 8 is a schematic cross-sectional view of another LMA device with an inflatable annular cuff inflated at a low pressure, in accordance with an application of the present invention.

Reference is now made to FIG. 8, which is a schematic cross-sectional view of an LMA device 600 with inflatable annular cuff 110 inflated at a low pressure, in accordance with an application of the present invention. For example, the low pressure may be 10 cm H2O. LMA device 600 comprises inflatable balloon 112 that is shaped so as to define inflatable annular cuff 110. Other than as described below, LMA device 600 is identical to LMA device 100, described hereinabove with reference to FIGS. 1-3D, and like reference numerals refer to like elements. The features of LMA device 600 may also be implemented in combination with the other LMA devices described herein, mutatis mutandis.

In this configuration, LMA device 600 comprises a single integral piece of material 602 that is shaped so as to define both a non-inflatable skeleton 640 and a backplate 630.

For some applications, the single integral piece of material 602 comprises a gel. Optionally, the single integral piece of material 602 further comprises a coating that coats the gel, such as a membrane.

For some applications, the single integral piece of material 602 has a Shore hardness of between A50 and A80.

Figure 9:
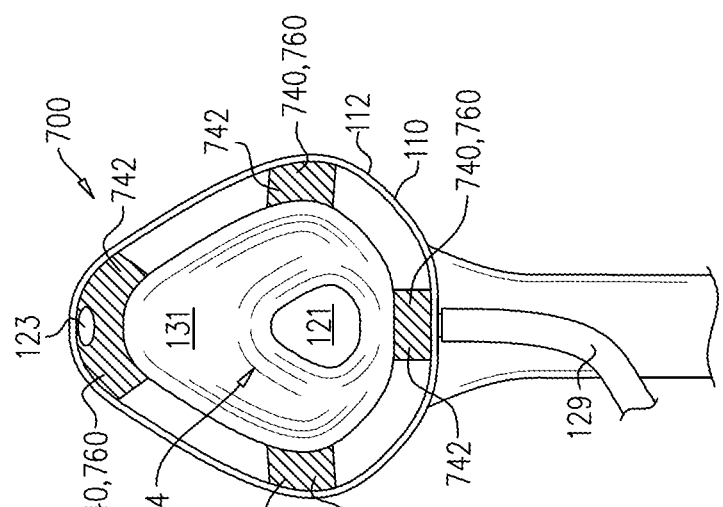
FIG. 9 is a schematic illustration of an anterior view of yet another LMA device with an inflatable annular cuff inflated at a low pressure, in accordance with an application of the present invention.

Reference is now made to FIG. 9, which is a schematic illustration of an anterior view of an LMA device 700 with inflatable annular cuff 110 inflated at a low pressure, in accordance with an application of the present invention. For example, the low pressure may be 10 cm H2O. LMA device 700 comprises inflatable balloon 112 that is shaped so as to define inflatable annular cuff 110. Other than as described below, LMA device 700 is identical to LMA device 100, described hereinabove with reference to FIGS. 1-3D, and like reference numerals refer to like elements. The features of LMA device 700 may also be implemented in combination with the other LMA devices described herein, mutatis mutandis.

As described hereinabove with reference to FIGS. 1-3D regarding LMA device 100, pre-formed shape 144 of skeleton anterior side 142 may be configured to provide a pre-inflation shape to inflatable annular cuff 110 when inflatable balloon 112 is not inflated. Similarly, LMA device 700 comprises a non-inflatable skeleton 740, which extends anteriorly from backplate 130, and which is shaped so as to define a skeleton anterior side 742 that has a pre-formed shape 744 that is configured to provide a pre-inflation shape to inflatable annular cuff 110 when inflatable balloon 112 is not inflated. Inflatable annular cuff 110 covers at least a portion of skeleton anterior side 742.

Non-inflatable skeleton 740 comprises a plurality of discrete, non-contiguous segments 760 around an anterior side of backplate 130. These discrete segments provide the pre-inflation shape to inflatable annular cuff 110 when inflatable balloon 112 is not inflated, even though non-inflatable skeleton 740 is not annular, i.e., does not define a complete, contiguous ring around the anterior side of backplate.

Figure 10:
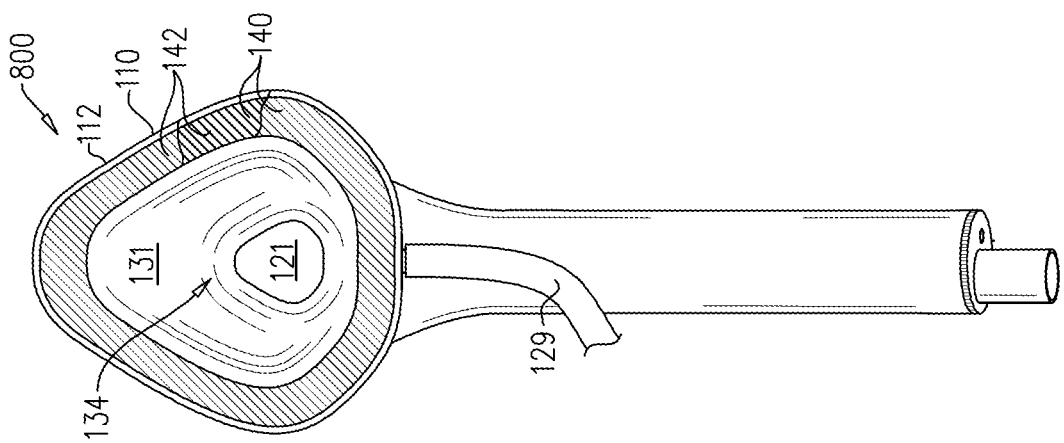
FIG. 10 is a schematic illustration of an anterior view of still another LMA device with an inflatable annular cuff inflated at a low pressure, in accordance with an application of the present invention.

Reference is now made to FIG. 10, which is a schematic illustration of an anterior view of an LMA device 800 with inflatable annular cuff 110 inflated at a low pressure, in accordance with an application of the present invention. For example, the low pressure may be 10 cm H2O. LMA device 800 comprises inflatable balloon 112 that is shaped so as to define inflatable annular cuff 110. Other than as described below, LMA device 800 is identical to LMA device 100, described hereinabove with reference to FIGS. 1-3D, and like reference numerals refer to like elements. The features of LMA device 800 may also be implemented in combination with the other LMA devices described herein, mutatis mutandis.

LMA device 800 is not shaped so as to define the above-mentioned gastric channel 128.

For some applications, such as shown in FIG. 10, inflatable annular cuff 110 covers an entirety of skeleton anterior side 142 (and optionally additional portions of non-inflatable skeleton 140, such as lateral surfaces thereof, and/or a portion of backplate 130).

Reference is made to FIGS. 2A-4D, 8, and 10. Although the following features are described below with reference to LMA device 100, described with reference to FIGS. 2A-3D, they may also be implemented in LMA devices 300, 600, and 800, described with reference to FIGS. 4A-D, 8, and 10, respectively.

As mentioned above, backplate 130 is shaped so as to define anterior laryngeal chamber region 131 and a posterior (pharyngeal) region 133 on the other, posterior side of backplate 130. For some applications, inflatable annular cuff 110 is shaped so as to define, around inflatable annular cuff 110:
 a first annular edge 160A (labeled in FIGS. 2A and 2D) that forms an airtight seal with anterior laryngeal chamber region 131 of backplate 130, and
 a second annular edge 160B (labeled in FIGS. 2B, 2C, and 2D) that forms an airtight seal with posterior region 133 of backplate 130.

It is noted that excess material of inflatable annular cuff 110 may extend beyond the annular edges; the annular edges are defined as the lines that form the airtight seals. For example, the airtight seals may be formed by heating, gluing, or pressing on with a rigid insert.

For some applications, LMA device 100 is configured such that when inflatable balloon 112 is disposed in free space and inflated to a pressure of 10 cm H2O, such as shown in FIGS. 2A-D, non-inflatable skeleton 140, along at least 25% (such as 50%, e.g., 75%) of a length of a curved central axis 162 (labeled in FIGS. 2A and 2D) of inflatable annular cuff 110, reaches to within 2 mm of or intersects curved central axis 162. Curved central axis 162 is the set of all centroids of transverse cross-sectional sections of inflatable annular cuff 110. Thus the cross-sectional sections are locally perpendicular to curved central axis 162, which runs along the inflatable annular cuff. In each transverse cross-sectional section of inflatable annular cuff 110 around inflatable annular cuff 110, one side 164 of inflatable annular cuff 110 is defined by a straight line segment between first annular edge 160A and second annular edge 160B. FIG. 2D shows two transverse cross-sectional sections of inflatable annular cuff 110 at different respective locations along curved central axis 162. It is noted that side 164 typically does not correspond to cuff-backplate interface surface 156, although it may.

Alternatively or additionally, for some applications, LMA device 100 is configured such that when inflatable balloon 112 is disposed in free space and inflated with air to a pressure of 10 cm H2O, such as shown in FIGS. 2A-D, along at least 25% (such as 50%, e.g., 75%) of a length of a curved central axis 162 (labeled in FIGS. 2A and 2D) of inflatable annular cuff 110, no more than 75% (e.g., no more than 50%) of a cross-sectional area of inflatable annular cuff 110 is filled with the air. In each transverse cross-sectional section of inflatable annular cuff 110 around inflatable annular cuff 110, one side 164 of inflatable annular cuff 110 is defined by a straight line segment between first annular edge 160A and second annular edge 160B.

Reference is made to FIGS. 5A-6D and 7A-D. Although the following features are described below with reference to LMA device 400, described with reference to FIGS. 5A-6D, they may also be implemented in LMA device 500, described with reference to FIGS. 7A-D. As described hereinabove, in these configurations, inflatable balloon 412 is shaped so as to define, in addition to inflatable annular cuff 410, a posterior portion 422 that covers at least a portion of a posterior region 133 of backplate 130, such as at least 75% of an area of posterior region 133, e.g., the entire posterior region 133.

For some applications, inflatable annular cuff 110 is shaped so as to define, around inflatable annular cuff 110, an annular edge 460 (labeled in FIGS. 5A and 5D) that forms an airtight seal with anterior laryngeal chamber region 131 of backplate 130.

For some applications, LMA device 100 is configured such that when inflatable balloon 112 is disposed in free space and inflated to a pressure of 10 cm H2O, such as shown in FIGS. 2A-D, non-inflatable skeleton 140, along at least 25% (such as 50%, e.g., 75%) of a length of a curved central axis 462 (labeled in FIGS. 2A and 2D) of inflatable annular cuff 410, reaches to within 2 mm of or intersects curved central axis 462. Curved central axis 462 is the set of all centroids of transverse cross-sectional sections of inflatable annular cuff 410. Thus the cross-sectional sections are locally perpendicular to curved central axis 462, which runs along the inflatable annular cuff. In each transverse cross-sectional section of inflatable annular cuff 410 around inflatable annular cuff 410, one side 464 of inflatable annular cuff 410 is defined by a straight line segment between (a) annular edge 460 and (b) a point 466 (labeled in FIG. 5D) on a surface of posterior region 133 closest to annular edge 460. FIG. 5D shows two transverse cross-sectional sections of inflatable annular cuff 410 at different respective locations along curved central axis 462. It is noted that side 464 typically does not correspond to cuff-backplate interface surface 156, although it may.

Alternatively or additionally, for some applications, LMA device 400 is configured such that when inflatable balloon 112 is disposed in free space and inflated with air to a pressure of 10 cm H2O, such as shown in FIGS. 5A-D, along at least 25% (such as 50%, e.g., 75%) of a length of a curved central axis 462 (labeled in FIGS. 5A and 5D) of inflatable annular cuff 410, no more than 75% (e.g., no more than 50%) of a cross-sectional area of inflatable annular cuff 410 is filled with the air. In each transverse cross-sectional section of inflatable annular cuff 410 around inflatable annular cuff 410, one side 464 of inflatable annular cuff 410 is defined by a straight line segment between (a) annular edge 460 and (b) point 466 (labeled in FIG. 5D) on a surface of posterior region 133 closest to annular edge 460.

In some applications of the prevent invention, methods are provided for ventilating the lungs of a patient. Although these methods may be implemented in any of the inflatable annular cuffs described herein, for the sake of brevity these methods are described for LMA device 100, described hereinabove with reference to FIGS. 1-3D.

A method is provided that comprises:
 inserting backplate 130, non-inflatable skeleton 140, and inflatable balloon 112 of LMA device 100 through a mouth of a patient and disposing, at an LMA-insertion location within a throat of the patient, inflatable annular cuff 110 defined by inflatable balloon 112, such that (a) a proximal end of inflation tube 129 is disposed outside the patient's mouth and (b) proximal end 120 of airway tube 125 of LMA device 100 is disposed outside the patient's mouth; and ventilating lungs of the patient using LMA device 100.

For some applications, pre-formed shape 144 of skeleton anterior side 142 is configured to provide a pre-inflation shape to inflatable annular cuff 110 when inflatable balloon 112 is not inflated, and the method further comprises inflating inflatable balloon 112 such that cuff anterior side 146 forms the seal around the laryngeal inlet of the patient.

For some applications, cuff anterior side 146 is configured to form the seal around the laryngeal inlet of the patient upon inflation of inflatable balloon 112 when inflatable annular cuff 110 is disposed at the LMA-insertion location, and the method further comprises inflating inflatable balloon 112 such that cuff anterior side 146 forms the seal around the laryngeal inlet of the patient.

For some applications, pre-formed shape 144 of skeleton anterior side 142 is configured to form an anatomical fit with the laryngeal inlet of the patient when inflatable annular cuff 110 is disposed at the LMA-insertion location. For some of these applications, cuff anterior side 146 is configured to form the seal around the laryngeal inlet of the patient even without inflation of inflatable balloon 112, when inflatable annular cuff 110 is disposed at the LMA-insertion location. For some of these applications, cuff anterior side 146 is configured such that the seal formed around the laryngeal inlet of the patient without inflation of inflatable balloon 112 provides a first level of sealing around the laryngeal inlet of the patient, and the method further comprises inflating inflatable balloon 112 such the seal formed around the laryngeal inlet of the patient provides a second level of sealing around the laryngeal inlet of the patient, the second level greater than the first.

For some of these applications:
backplate 130, non-inflatable skeleton 140, and inflatable balloon 112 are inserted without inflating inflatable balloon 112,
ventilating the lungs comprises applying a first level of ventilation while inflatable balloon 112 is not inflated and the seal formed around the laryngeal inlet of the patient thus provides the first level of sealing around the laryngeal inlet of the patient,
inflating inflatable balloon 112 comprises inflating inflatable balloon 112 after beginning applying the first level of ventilation, and
the method further comprises, after inflating inflatable balloon 112, applying a second level of ventilation that is greater than the first level of ventilation and thus requires the greater second level of sealing around the laryngeal inlet of the patient.

For some applications:
cuff anterior side 146 is configured such that the seal formed around the laryngeal inlet of the patient without inflation of inflatable balloon 112 provides a first level of sealing around the laryngeal inlet of the patient,
backplate 130, non-inflatable skeleton 140, and inflatable balloon 112 are inserted without inflating inflatable balloon 112,
ventilating the lungs comprises applying a desired level of ventilation while inflatable balloon 112 is not inflated and the seal formed around the laryngeal inlet of the patient thus provides the first level of sealing around the laryngeal inlet of the patient, and the method further comprises (a) after beginning ventilating the lungs, ascertaining whether the first level of sealing is sufficient for the desired level of ventilation; and (b) upon ascertaining the first level of sealing is not sufficient for the desired level of ventilation, inflating inflatable balloon 112 such that cuff anterior side 146 the seal formed around the laryngeal inlet of the patient provides a second level of sealing around the laryngeal inlet of the patient, the second level greater than the first and sufficient for the desired level of ventilation.

Figure 11D:
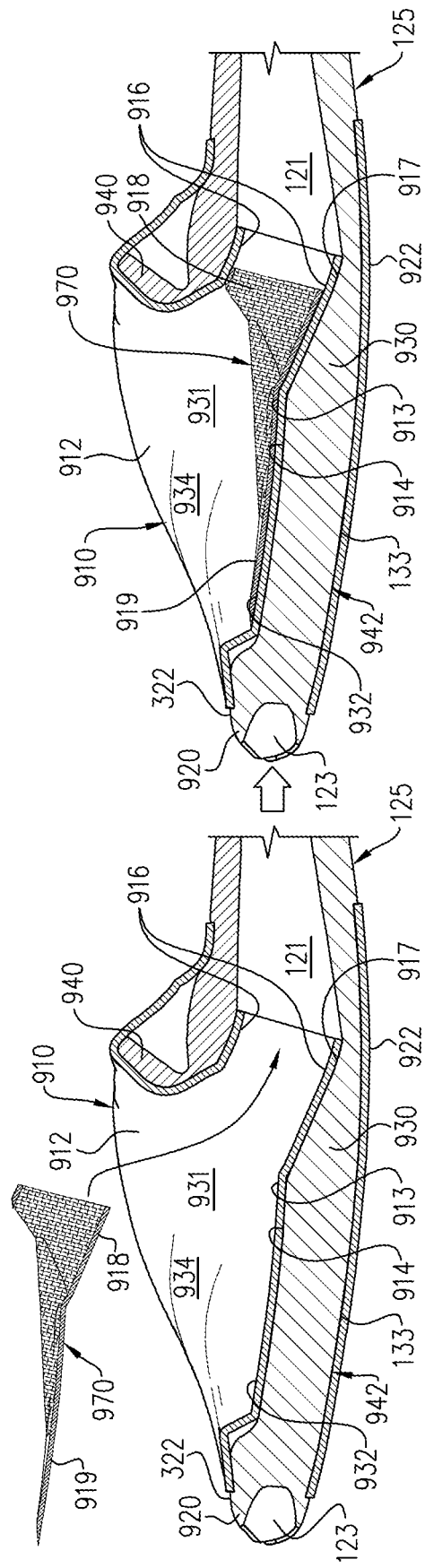

Reference is now made to FIGS. 11A-D, which are schematic illustrations of respective views of an LMA device 900 with an inflatable annular cuff 910 inflated at a low pressure, in accordance with an application of the present invention. FIGS. 11A, 11B, and 11C are anterior, side, and anterior views of LMA device 900, respectively, and FIG. 11D is a cross-sectional view take along lines XID-XID of FIG. 11C. For example, the low pressure may be 10 cm H2O. Other than as described below, LMA device 900 is similar to LMA device 500, described hereinabove with reference to FIGS. 7A-D, and like reference numerals refer to like elements. The features of LMA device 900 may also be implemented in combination with the other LMA devices described herein, mutatis mutandis. Typically, LMA device 900 does not comprise inflation port 126 on inflatable annular cuff 910, and a distal end of inflation tube 129 is coupled in fluid communication with (i) an interior of an inflatable balloon 912 of LMA device 900 and (ii) at least a portion of skeleton anterior side 942, described hereinbelow.

Figure 12C:
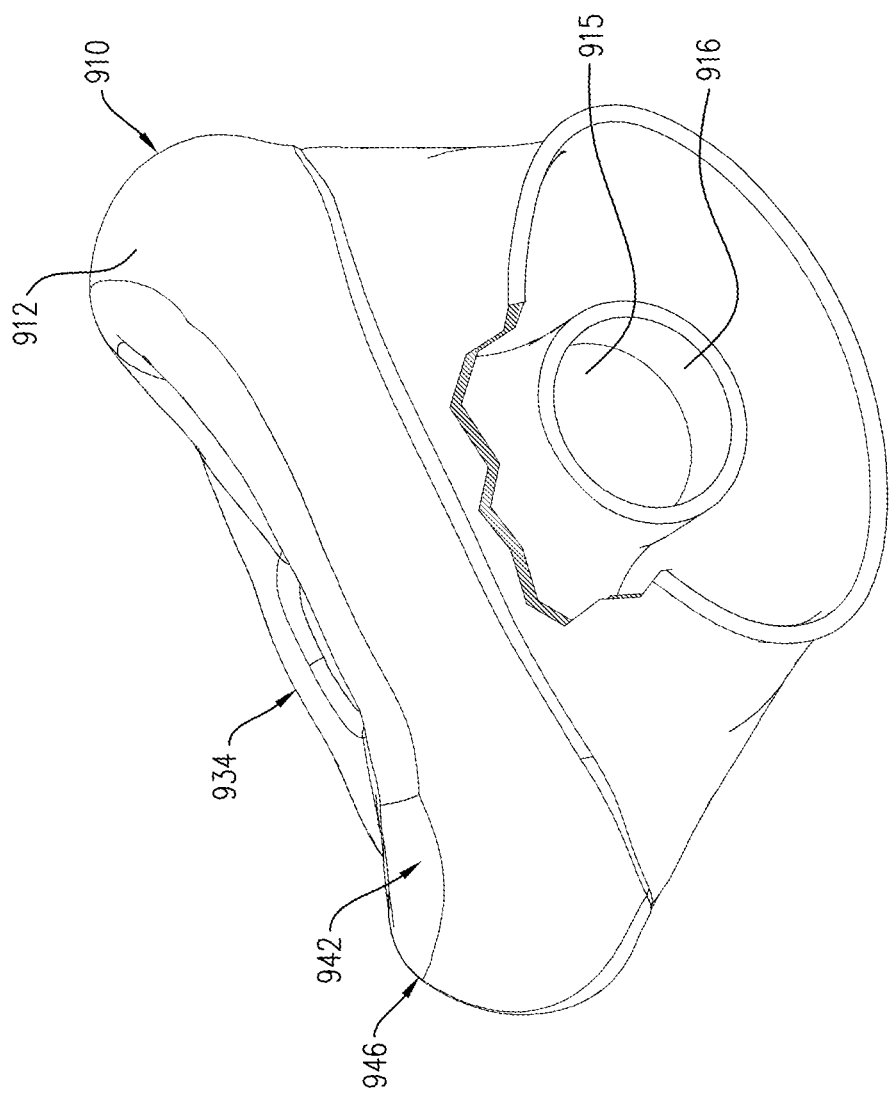

Reference is further made to FIGS. 12A-C, which are schematic illustrations of several views of inflatable balloon 912, in accordance with an application of the present invention.

Figure 13B:
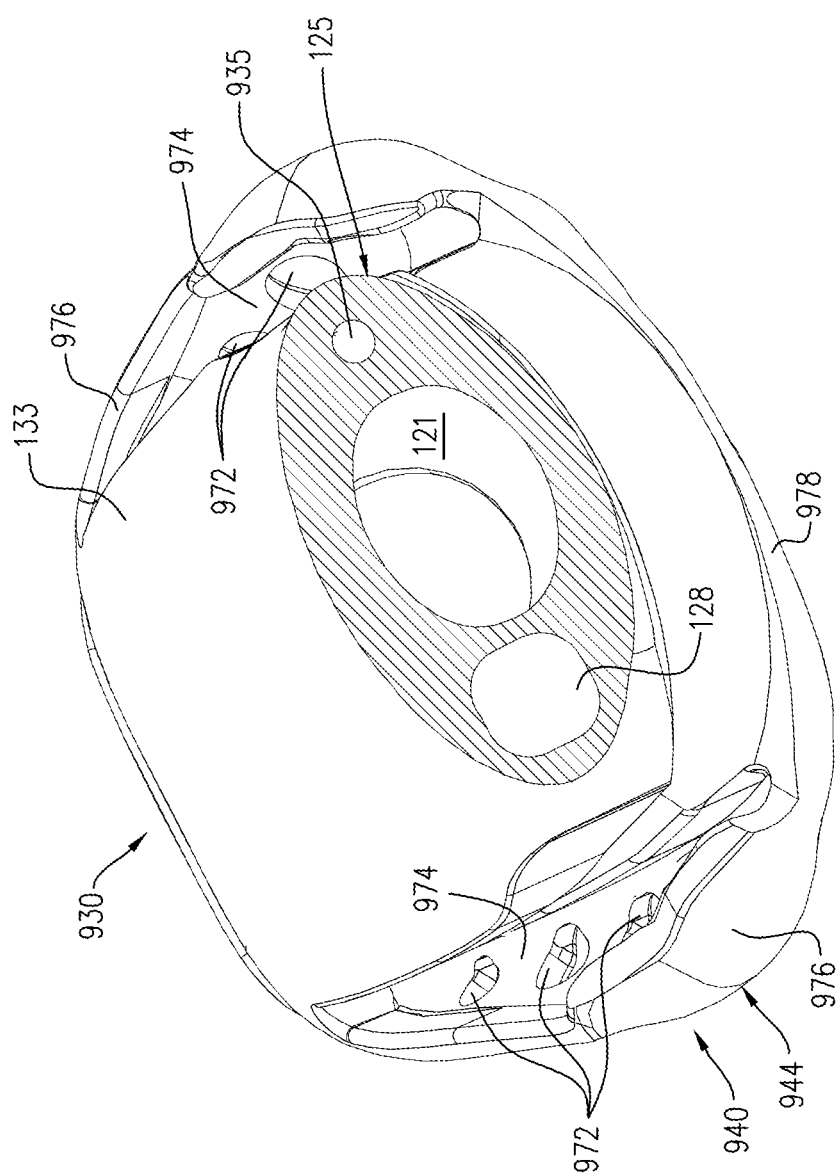

Reference is still further made to FIGS. 13A-B, which are schematic illustrations of two views of a non-inflatable skeleton 940 and a portion of airway tube 125 of LMA device 900, in accordance with an application of the present invention. (A channel 935 is in fluid communication with inflation tube 129 and the interior of inflatable balloon 912.)

LMA device 900 comprises:
inflatable balloon 912, which is shaped so as to define inflatable annular cuff 910;
non-inflatable skeleton 940, which extends anteriorly from backplate 930, is shaped so as to define a skeleton anterior side 942 that has a pre-formed shape 944, and may implement any of the features of non-inflatable skeletons 140, 640, and/or 740 described herein; and
a backplate 930, which has backplate airway port 121 and may implement any of the features of backplates 130 and/or 630 described herein.

Backplate 930 is shaped so as to define an anterior laryngeal chamber region 931 into which backplate airway port 121 is open. Backplate airway port 121 is open through a cuff opening 934 through inflatable annular cuff 910, i.e., through the central open space surrounded by the annulus of inflatable annular cuff 910. Inflatable annular cuff 910 has a cuff anterior side 946 that is configured to form a seal around a laryngeal inlet of the patient when inflatable annular cuff 910 is disposed at an LMA-insertion location within a throat of the patient.

Inflatable balloon 912 is shaped so as to define an anterior-laryngeal-chamber-region covering portion 913 that:
is open to cuff opening 934,
covers a chamber-region surface 914 defined by anterior laryngeal chamber region 931, and is shaped so as to define a covering-portion opening 915 (labeled in FIGS. 12B and 12C, described hereinbelow) in fluid communication with cuff opening 934 and backplate airway port 121.

Typically, inflatable balloon 912 forms an airtight seal between covering-portion opening 915 and backplate airway port 121.

For some applications, LMA device 900 further comprises a balloon-restraining insert 970, which (a) presses (typically snugly) anterior-laryngeal-chamber-region covering portion 913 of inflatable balloon 912 against chamber-region surface 914, thereby inhibiting (e.g., preventing) inflation of anterior-laryngeal-chamber-region covering portion 913 of inflatable balloon 912, and (b) is disposed partially within backplate airway port 121 (labeled in FIG. 11D).

For some applications, inflatable balloon 912 is shaped so as to define a balloon tubular portion 916 (labeled in FIGS. 11D and 12C). Balloon-restraining insert 970 presses balloon tubular portion 916 against an internal surface 917 (labeled in FIG. 11D) of backplate airway port 121, such that inflatable balloon 912 forms the airtight seal between covering-portion opening 915 and backplate airway port 121. For some applications, balloon-restraining insert 970 is shaped so as to define an insert tubular portion 918, which presses balloon tubular portion 916 against internal surface 917 of backplate airway port 121. Optionally, insert tubular portion 918 is coupled to internal surface 917 of backplate airway port 121 by friction. Alternatively or additionally, the airtight seal between covering-portion opening 915 and backplate airway port 121 is formed by gluing, welding, and/or otherwise adhering insert tubular portion 918 to internal surface 917 of backplate airway port 121, and/or insert tubular portion 918 is coupled to internal surface 917 of backplate airway port 121 by gluing, welding, and/or otherwise adhering insert tubular portion 918 to internal surface 917 of backplate airway port 121.

For some applications, balloon-restraining insert 970 is shaped so as to define a tab 919 that is in contact with a portion 932 of anterior-laryngeal-chamber-region covering portion 913 so as to press anterior-laryngeal-chamber-region covering portion 913 against chamber-region surface 914. For some applications, a contact area between tab 919 and portion 932 of anterior-laryngeal-chamber-region covering portion 913 is at least 1 cm2, no more than 6 cm2, and/or between 1 and 6 cm2.

For some applications, portion 932 is recessed in anterior-laryngeal-chamber-region covering portion 913. Further optionally, non-inflatable skeleton 940 is shaped so as to define a corresponding indentation for insertion of portion 932 and tab 919 (optionally, the corresponding indentation is shaped so as to enable snapping of tab 919 into the indentation during assembly of LMA device 900 during manufacture thereof).

For some applications, inflatable balloon 912 is shaped so as to define, in addition to inflatable annular cuff 910 and anterior-laryngeal-chamber-region covering portion 913, a posterior portion 922 that covers at least a portion of posterior region 133 of backplate 930. Posterior portion 922 may have any of the features of posterior portion 422 described hereinabove.

Alternatively or additionally, for some applications, LMA device 900 is shaped so as to define gastric channel 128 having distal gastric opening 123 through distal tip portion 920 of non-inflatable skeleton 940. LMA device 900 may implement any of the features of LMA devices 100 and/or 400, described hereinabove, regarding distal gastric opening 123, or LMA devices 300 and/or 500, described hereinabove, regarding distal tip portion 320 and the attachment of the annular cuff to the non-inflatable skeleton.

For some applications, non-inflatable skeleton 940 separates and prevents at least some opposing interior portions of inflatable annular cuff 910 from coming into contact with one another when inflatable balloon 912 is deflated at a negative pressure (e.g., at suction pressure of negative 30 cm H2O (−30 cm H2O)).

Reference is made to FIGS. 11B and 13A-B. For some applications, non-inflatable skeleton 940 is shaped so as to define one or more holes 972 (e.g., two or more holes 972, such as between two and ten holes 972) between skeleton anterior side 942 and an interior skeleton surface 974 of non-inflatable skeleton 940. Both skeleton anterior side 942 and an interior skeleton surface 974 are in fluid communication with the interior of inflatable balloon 912. Holes 972 help with air distribution within inflatable balloon 912 upon inflation thereof, by allowing air to pass from an interior portion of non-inflatable skeleton 940 to skeleton anterior side 942. Typically, each of holes 972 has a cross-sectional area of at least 1 mm2, no more than 10 mm2, and/or between 1 mm2 and 10 mm2. The other LMA devices described herein may also implement the features described in this paragraph, mutatis mutandis.

Figure 14A:
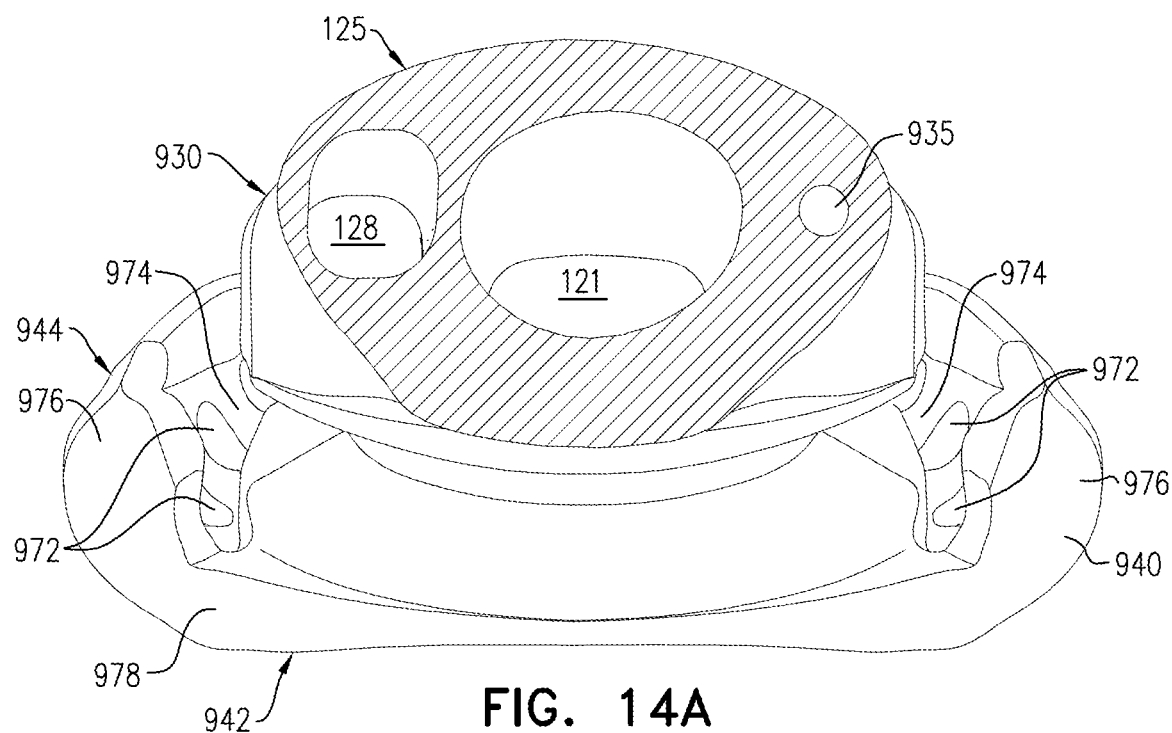
FIGS. 14A and 14B are schematic illustrations of portions of a non-inflatable skeleton, a backplate, and an airway tube of the LMA device of FIGS. 11A-D with the non-inflatable skeleton in a resting and laterally compressed states, respectively, in accordance with an application of the present invention.
Figure 14B:
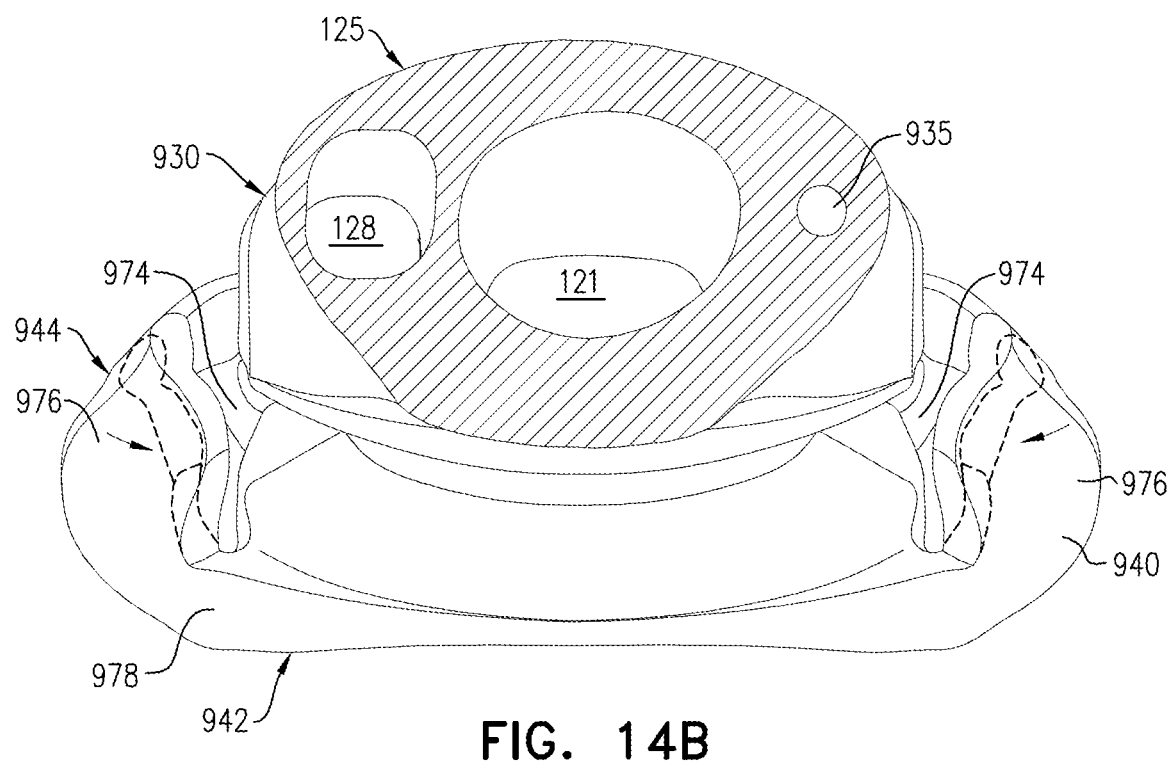

Reference is now made to FIGS. 14A and 14B, which are schematic illustrations of portions of non-inflatable skeleton 940, backplate 930, and airway tube 125 of LMA device 900 with non-inflatable skeleton 940 in resting and laterally compressed states, respectively, in accordance with an application of the present invention.

Figure 15A:
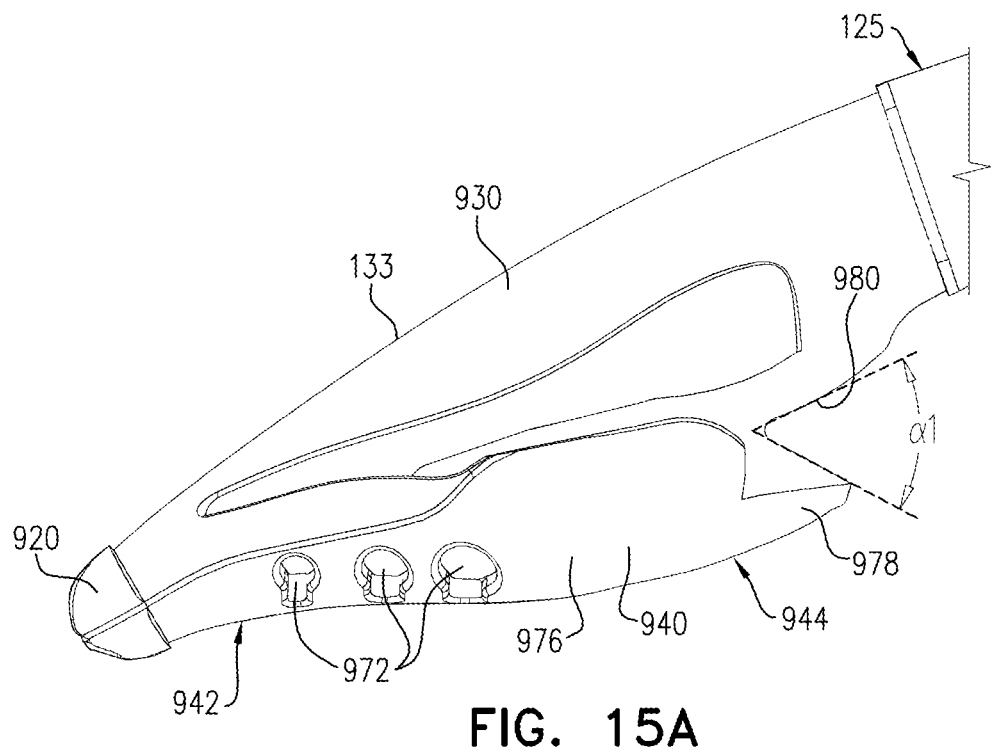
FIGS. 15A and 15B are schematic illustrations of portions of a non-inflatable skeleton, a backplate, and an airway tube of the LMA device of FIGS. 11A-D with the non-inflatable skeleton in a resting and posteriorly compressed states, respectively, in accordance with an application of the present invention.
Figure 15B:
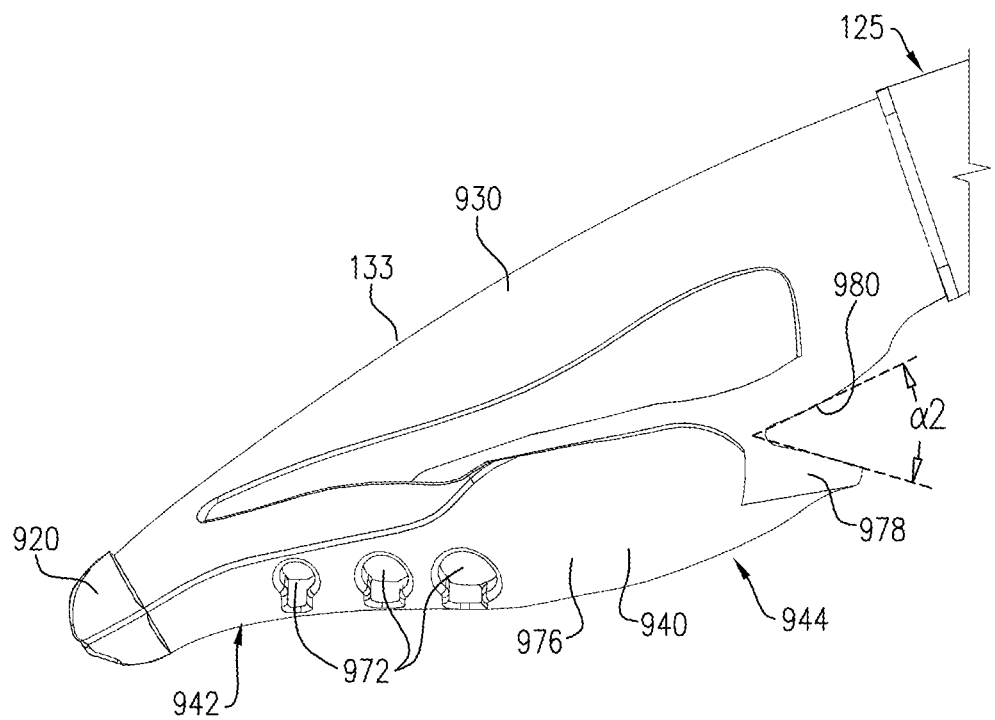

Reference is further made to FIGS. 15A and 15B, which are schematic illustrations of portions of non-inflatable skeleton 940, backplate 930, and airway tube 125 of LMA device 900 with non-inflatable skeleton 940 in resting and posteriorly compressed states, respectively, in accordance with an application of the present invention.

Reference is still further made to FIGS. 13A and 13B, which show non-inflatable skeleton 940 in the resting state.

In this configuration, at least a portion of non-inflatable skeleton 940 is shaped so as to define one or more wings 976 (e.g., exactly two wings 976, as shown in the figures). Wings 976 are partially connected to (typically integral to) backplate 930 and/or non-wing portions of non-inflatable skeleton 940, and non-connected portions of wings 976 are configured to flex with respect to backplate 930, when a force is applied to the wings, such as by the anatomy of the patient. Wings 976 provide in part the pre-formed shape 944 of non-inflatable skeleton 940 shown in FIGS. 14A and 15A and other figures, and also provide some flexibility to non-inflatable skeleton 940 such that the skeleton is not excessively stiff. Wings 976 are shaped so as to define the above-mentioned interior skeleton surface 974. Optionally, wings 976 are shaped so as to define the above-mentioned holes 972; alternatively, wings 976 are not shaped so as to define the holes. The other LMA devices described herein optionally may also implement wings 976, mutatis mutandis.

As shown in FIGS. 14B and 15B and as mentioned above, wings 976 are configured to flex with respect to backplate 930, when a force is applied to the wings, such as by the anatomy of the patient. In the configuration shown in FIGS. 14A and 14B, wings 976 are configured to laterally flex with respect to backplate 930 when a lateral force is applied to the wings, such as by the anatomy of the patient. In the configuration shown in FIGS. 15A and 15B, a proximal portion 978 of wings 976 is configured to posteriorly flex with respect to backplate 930 when a posteriorly-directed force is applied to the wings, such as by the anatomy of the patient. For example, an angle α (alpha) between proximal portion 978 of wings 976 and a posterior surface 980 may decrease from α1 to α2 when the posteriorly-directed force is applied to the wings. Wings 976 may be configured to allow both or a single one of the types of flexing described in FIGS. 14A-B and FIGS. 15A-B.

Figure 16A:
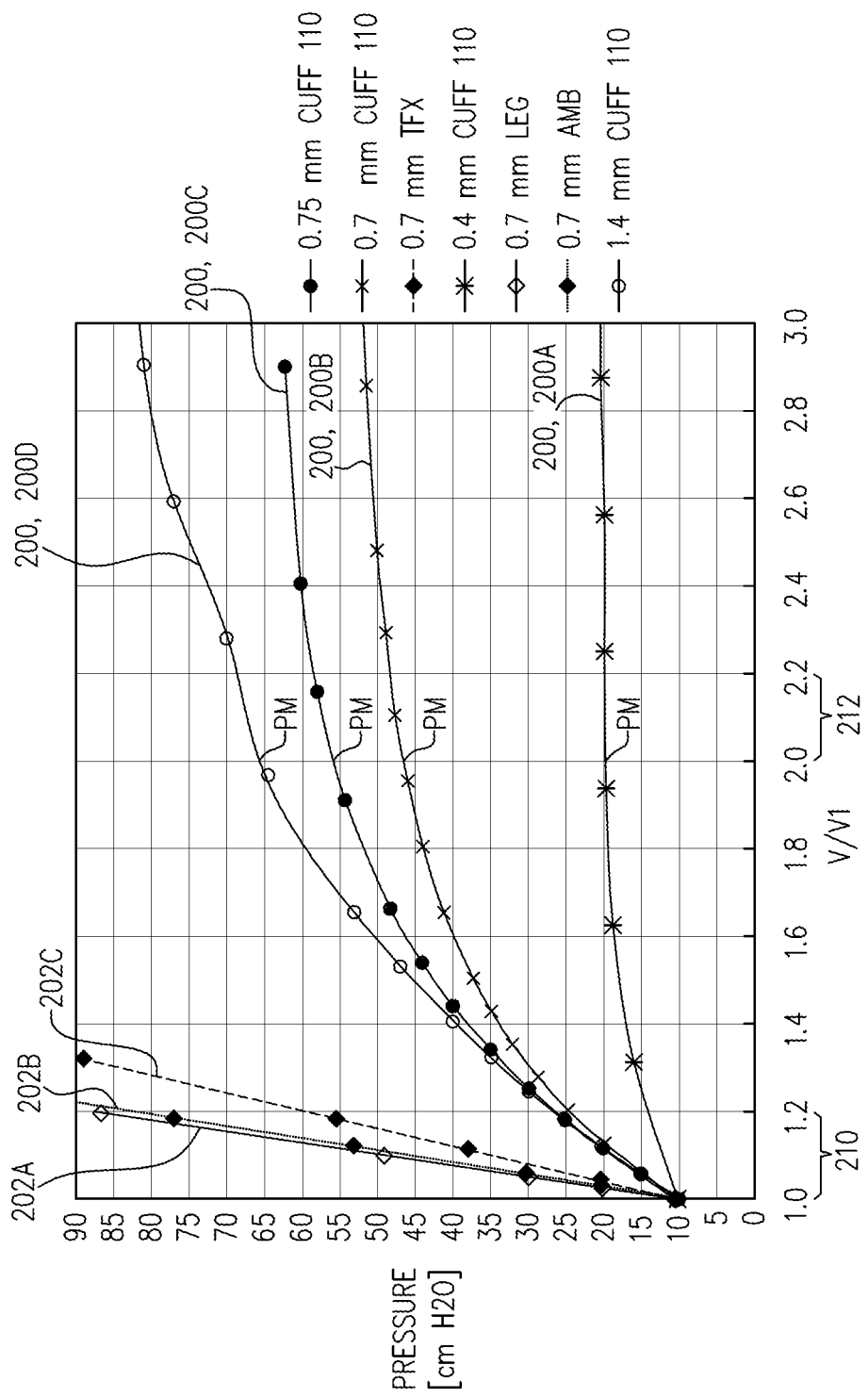
FIGS. 16A-B include several pressure-volume curves, some in accordance with an application of the present invention and others of devices in the prior art.
Figure 16B:
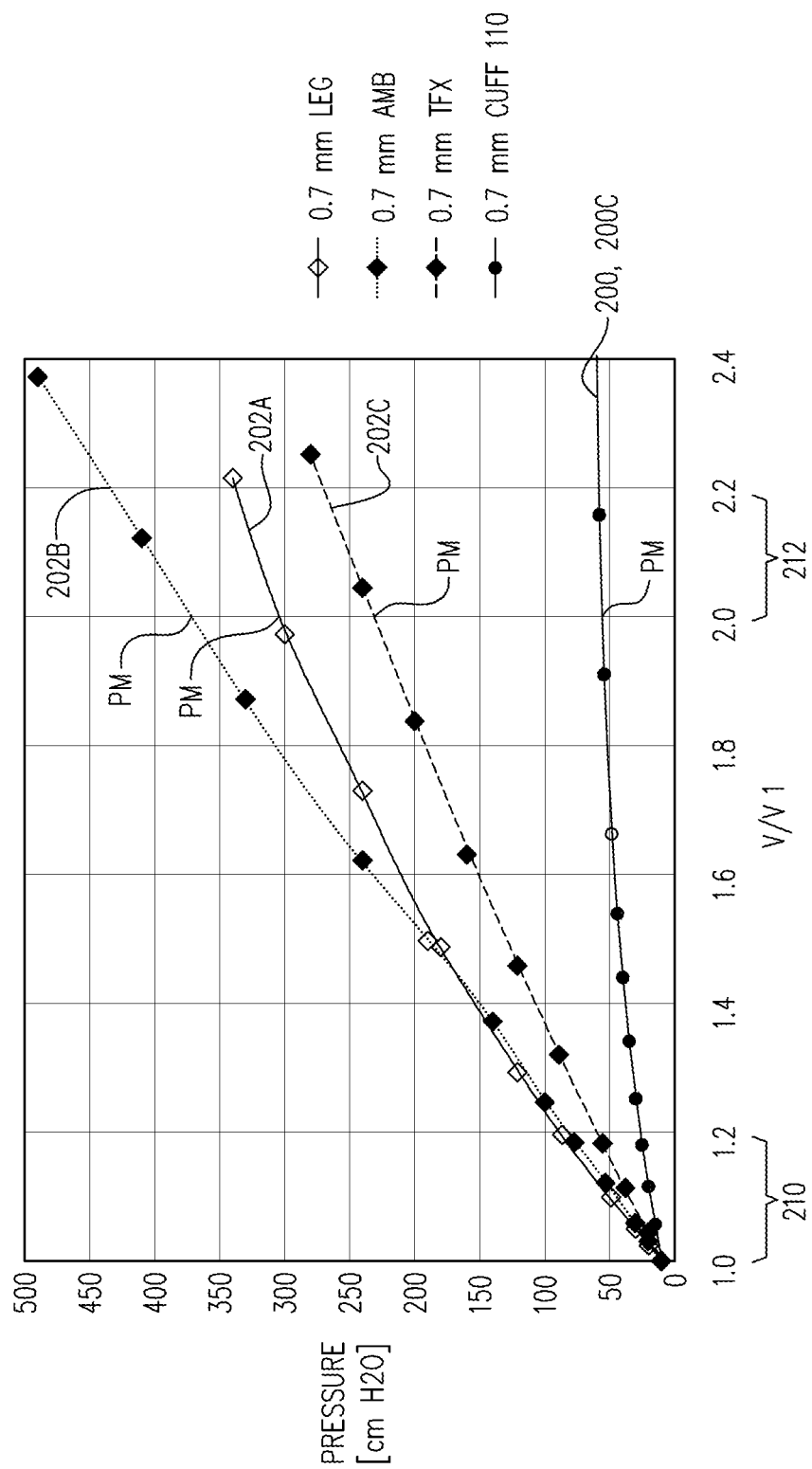

Reference is now made to FIGS. 16A-B, which include several pressure-volume curves 200, some in accordance with an application of the present invention and others of devices in the prior art. FIGS. 16A and 16B include different pressure ranges. Although the techniques described with reference to FIGS. 16A and 16B may be implemented in any of the inflatable annular cuffs described herein, for the sake of brevity these techniques are described for inflatable annular cuff 110, described hereinabove with reference to FIGS. 1-3D.

Inflatable annular cuff 110, when disposed in free space, is characterized by a pressure-volume curve 200, which represents the pressure in inflatable annular cuff 110 when inflated, from a deflated negative pressure (e.g., −30 cm H2O), to different volumes of ambient-pressure air, which include a low-pressure volume V1 that results in a low pressure of 10 cm H2O. Pressure-volume curves 200 illustrated in FIG. 16A include exemplary pressure-volume curves 200A, 200B, 200C, and 200D, and in FIG. 16B include only exemplary pressure-volume curve 200C; a large number of additional pressure-volume curves having the general properties of pressure-volume curves 200 are possible, and are within the scope of the present invention. Exemplary pressure-volume curves 200A, 200B, 200C, and 200D are based on measurements made by the inventors using cuffs 110 having average wall thicknesses of 0.4 mm, 0.7 mm, 0.75 mm, and 1.4 mm, respectively. The low-pressure volumes V1 of air are defined as the quantities of ambient-pressure air added to inflatable annular cuff 110 when initially substantially empty of air, i.e., containing a negligible quantity of air when emptied at a deflated negative pressure of −30 cm H2O. These first volumes V1 served as baselines for comparison with pressures achieved upon additional inflation of the cuffs.

FIGS. 16A-B also include exemplary known pressure-volume curves 202A, 202B, and 202C, measured by the inventors using the following known LMA cuffs:
  pressure-volume curves 202A: a Legend M.D.™ LMA106 size #4 laryngeal mask device cuff (Legend Medical Devices, City of Industry, Calif., USA), having an average wall thickness of 0.7 mm,
  pressure-volume curves 202B: an Ambu® AuraOnce™ size #4 laryngeal mask device cuff (Ambu A/S, Ballerup, Denmark), having an average wall thickness of 0.7 mm, and
  pressure-volume curves 202C: an LMA Supreme™ size #4 laryngeal mask device cuff (Teleflex Inc., Wayne, Pa., USA), having an average wall thickness of 0.7 mm.
Each of pressure-volume curves 200 includes:
  a low-pressure-range average rate of change over a low-pressure volume interval 210 between 1.0 and 1.2 times the low-pressure volume V1,
  a medium-pressure-range average rate of change over a medium-pressure volume interval 212 between 2.0 and 2.2 times the low-pressure volume V1, and
  a working medium pressure $P_M$ at a working medium volume of the cuff equal to 2.0 times the low-pressure volume V1.

In the present application, including in the claims and Inventive concepts, the "average rate of change" is the slope of the secant line joining respective points on the curve at the endpoints of the relevant interval, as is known in the mathematical arts.

For some applications, the medium-pressure-range average rate of change is less than 0.5 times the low-pressure-range average rate of change, such as less than 0.4 times, or less than 0.2 times, the low-pressure-range average rate of change.

Alternatively or additionally, for some applications, the medium-pressure-range average rate of change is between 1 and 25 cm H2O, such as between 5 and 20 cm H2O, e.g., between 10 and 20 cm H2O. The low-pressure volume V1 (that results in the low pressure of 10 cm H2O) is typically about 20 cc (typically with a +/−5 cc variation range). Therefore, the average rate of change (i.e., slope) is divided by 20 to convert to physical inflation by cubic centimeters of air. As a result, in pressure-volume curves 200 a slope of 20 cm H2O is approximately an inflation rate of change of 1 cm H2O per cc of air inflation. This implies that movements of inflatable annular cuff 110 that compress or expand the cuff by +/−1 cc will result in only a small variation of the cuff pressure of +/−1 cm H2O. It is desired to avoid substantial changes in the cuff pressure, since high pressure can lead to patient soft tissue damage and low pressure compromises the air seal effectiveness for ventilating the patient. In contrast, conventional LMA cuffs, as demonstrated in the experimental data presented herein, have pressure-volume curves with average rates of changes (i.e., slopes) greater than 100 cm H2O, i.e., an approximate inflation a rate of change greater than 5 cm H2O per cc of air inflation.

For some applications, the low-pressure-range average rate of change is between 15 and 100 cm H2O, such as between 20 and 50 cm H2O.

Typically, the working medium pressure $P_M$ is between 20 and 200 cm H2O, such as between 20 and 120 cm H2O, e.g., between 20 and 70 cm H2O, such as between 20 and 40 cm H2O.

Typically, pressure-volume curve 200 does not have any local maximums at any volumes less than 3 times the low-pressure volume V1.

In order to provide pressure-volume curves 200 described above, inflatable annular cuff 110 comprises a highly elastic material that results in substantial expansion of the cuff upon incremental inflation. For example, inflatable annular cuff 110 may comprise non-latex synthetic polyisoprene, e.g., primarily non-latex synthetic polyisoprene by weight; for some applications, the average thickness of a wall of inflatable annular cuff 110 is between 0.5 and 1.5 mm, such as between 0.6 and 0.9 mm, at all non-attached locations of inflatable annular cuff 110 that are not attached to backplate 130. Alternatively, for example, inflatable annular cuff 110 may comprise silicone, e.g., primarily silicone by weight; for some applications, the average thickness of the wall of inflatable annular cuff 110 is between 0.5 and 1.5 mm, such as between 0.6 and 0.9 mm, at all non-attached locations of inflatable annular cuff 110 that are not attached to backplate 130; alternatively or additionally, for some applications, the silicone has a hardness of less than Shore A30, or less than Shore OO-80, or less than Shore OO-60.

By contrast, conventional LMA devices employ cuffs having little elasticity at the working inflation pressure range.

For some applications, inflatable annular cuff 110 is configured such that when disposed in free space and inflated, from the deflated negative pressure, by the low-pressure volume V1, further inflation of inflatable annular cuff 110 with an incremental quantity of air results in a pressure in inflatable annular cuff 110 that is less than 25 cm H2O, the incremental quantity of air having a volume, when the air is at ambient pressure, equal to 10% of the low-pressure volume V1.

For some applications, inflatable annular cuff 110 is configured such that when disposed in free space and inflated, from the deflated negative pressure, by the low-pressure volume V1, further inflation of inflatable annular cuff 110 with an incremental quantity of air results in a pressure in inflatable annular cuff 110 that is less than 35 cm H2O, the incremental quantity of air having a volume, when the air is at ambient pressure, equal to 20% of the low-pressure volume V1.

By contrast, cuff pressure in the known cuffs continuously increased with increases of inflation volume. At additional inflation volumes of as little as 20% of the respective first volumes V1, the pressures in the known cuffs rose to high levels that might cause soft tissue ischemia during ordinary use. This occurs because knowns cuffs substantially attain their working volumes at low inflation pressures, such as 10 cm H2O. Further inflation by an additional 10% to 30% of the inflation volume that resulted in the pressure of 10 cm H2O results in only a small increase of the cuff volume and a large increase (typically greater than 100%) in the cuff pressure.

Reference is still made to FIGS. 16A-B. During use of LMA device 100 after inflatable annular cuff 110 has been placed at the LMA-insertion location, as shown in FIG. 1, when it is necessary to inflate inflatable annular cuff 110 to provide an adequate seal, inflatable annular cuff 110 is ideally inflated to a pressure greater than 20 cm H2O (e.g., greater than 25 cm H2O, such as greater than 30 cm H2O) and less than 60 cm H2O.

In practice, the healthcare worker often inflates inflatable annular cuff 110 with a known quantity of ambient-pressure air, rather than to a certain pressure, because the pressure is typically not measured during or after inflation of inflatable annular cuff 110. Also, often the healthcare worker may inflate the cuff outside the patient's mouth and then press the cuff into the patient's throat. Consequently, in conventional devices, there are often significant pressure variations in the outcome of inflation pressure compared with the intended target pressure.

LMA device 100 is typically accompanied by instructions for use that specify a narrow range of quantities of ambient-pressure air, e.g., 25 to 30 cc for a standard adult-size cuff. The range of air quantities is ascertained by the manufacturer for each configuration of LMA device 100, based in large part on pressure-volume curve 200 of inflatable annular cuff 110. Ideally, the specified range of quantities of air would result in a fixed pressure volume range. However, in practice the variation in human throat size and shape results in substantial variation in the cuffs actual size when in place, and movement of the patient may shift the cuffs positioning within the throat. Yet, because of the shapes of pressure-volume curves 200 of inflatable annular cuff 110, moderate underinflation and even substantial over-inflation still results in a working medium pressure $P_M$ that is suitable for facilitating lung ventilation, without any need to adjust the inflation of the cuff.

As mentioned above, one of pressure-volume curves 200 characterizes inflatable annular cuff 110 when disposed in free space. Nevertheless, when the cuff is placed at the LMA-insertion location, the constraints of the anatomy on the cuff typically have only minimal impact on the pressure-volume curve of the cuff, and do not materially increase the pressure in the cuff. By contrast, in conventional LMA devices, such constraints generally lead to a significant increase (e.g., by more than 25%, or more than 50%) of the cuff pressure compared to pressure achieved at the same inflation volume when the cuff is disposed in free space.

In the present application, including in the claims, all pressures are gauge pressures that are zero-referenced against ambient air 99 pressure.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

In an embodiment, techniques and apparatus described in one or more of the following applications, which are assigned to the assignee of the present application and incorporated herein by reference, are combined with techniques and apparatus described herein:

U.S. Provisional App. No. 62/592,020, filed Nov. 29, 2017

U.S. application Ser. No. 15/878,993, filed Jan. 24, 2018, now U.S. Pat. No. 10,369,311

U.S. application Ser. No. 15/951,564, filed Apr. 12, 2018, now U.S. Pat. No. 10,173,022

U.S. Provisional App. No. 62/789,208, filed Jan. 7, 2019

International Appl. No. PCT/IL2018/051306, filed Nov. 29, 2018, which published as PCT Publication WO 2019/106670

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A laryngeal mask airway device comprising:
   a backplate, which is (a) shaped so as to define a backplate airway port, and (b) insertable through the mouth of a patient;
   an inflatable balloon, which is shaped so as to define an inflatable annular cuff;
   an airway tube having (a) a proximal end that is configured to be disposed outside the patient's mouth when the inflatable annular cuff is disposed at a laryngeal-mask-airway-insertion location, and (b) a distal end that is in fluid communication with the backplate airway port; and
   a non-inflatable skeleton, which extends anteriorly from the backplate, and which is shaped so as to define a skeleton anterior side that has a pre-formed shape; and
   an inflation tube having (a) a proximal end that is configured to be disposed outside the patient's mouth when the inflatable annular cuff is disposed at the laryngeal-mask-airway-insertion location, and (b) a distal end that is coupled in fluid communication with (i) an interior of the inflatable balloon for supplying air to the inflatable balloon, and (ii) at least a portion of the skeleton anterior side,
   wherein the inflatable annular cuff (a) covers at least a portion of the skeleton anterior side, and (b) has a cuff anterior side that is configured to form a seal around a laryngeal inlet of the patient when the inflatable annular cuff is disposed at the laryngeal-mask-airway-insertion location within the throat of the patient, wherein the backplate airway port is open through a cuff opening through the inflatable annular cuff, wherein the laryngeal mask airway device is shaped so as to define a gastric channel having a distal gastric opening through a distal tip portion of the non-inflatable skeleton, an anterior side of the distal tip portion having an area equal to less than 20% of a total area of the skeleton anterior side, and wherein the inflatable annular cuff covers an entirety of the skeleton anterior side other than the anterior side of the distal tip portion of the non-inflatable skeleton.

2. The laryngeal mask airway device according to claim 1, wherein the non-inflatable skeleton separates and prevents at least some opposing interior portions of the inflatable annular cuff from coming into contact with one another when the inflatable balloon is deflated at a negative pressure.

3. The laryngeal mask airway device according to claim 1, wherein the laryngeal mask airway device comprises a single integral piece of material that is shaped so as to define both the non-inflatable skeleton and the backplate.

4. The laryngeal mask airway device according to claim 1, wherein the pre-formed shape is configured to provide a pre-inflation shape to the inflatable annular cuff when the inflatable balloon is not inflated.

5. The laryngeal mask airway device according to claim 1, wherein the cuff anterior side is configured to form the seal around the laryngeal inlet of the patient upon inflation of the inflatable balloon when the inflatable annular cuff is disposed at the laryngeal-mask-airway-insertion location.

6. The laryngeal mask airway device according to claim 1, wherein the pre-formed shape is configured to form an anatomical fit with the laryngeal inlet of the patient when the inflatable annular cuff is disposed at the laryngeal-mask-airway-insertion location.

7. The laryngeal mask airway device according to claim 6, wherein the cuff anterior side is configured to form the seal around the laryngeal inlet of the patient even without inflation of the inflatable balloon, when the inflatable annular cuff is disposed at the laryngeal-mask-airway-insertion location.

8. The laryngeal mask airway device according to claim 7, wherein the cuff anterior side is configured such that:
the seal formed around the laryngeal inlet of the patient without inflation of the inflatable balloon provides a first level of sealing around the laryngeal inlet of the patient, and
a seal formed around the laryngeal inlet of the patient upon inflation of the inflatable balloon to a pressure of 30 cm H2O when the inflatable annular cuff is disposed at the laryngeal-mask-airway-insertion location provides a second level of sealing around the laryngeal inlet of the patient, the second level greater than the first.

9. The laryngeal mask airway device according to claim 1, wherein an internal surface of the inflatable annular cuff and an external surface of the non-inflatable skeleton together define an inflatable chamber between the inflatable annular cuff and the non-inflatable skeleton.

10. The laryngeal mask airway device according to claim 9, wherein the laryngeal mask airway device is configured such that when the inflatable balloon is disposed in free space and inflated to a pressure of 10 cm H2O:
the internal surface of the inflatable annular cuff that helps define the inflatable chamber has an internal surface area, and
the external surface of the non-inflatable skeleton that helps define the inflatable chamber has an external surface area equal to at least 25% of the internal surface area.

11. The laryngeal mask airway device according to claim 1, wherein the inflatable balloon is shaped so as to define, in addition to the inflatable annular cuff, a posterior portion that covers at least a portion of a posterior region of the backplate.

12. The laryngeal mask airway device according to claim 11, wherein the inflatable balloon is shaped such that respective interiors of the inflatable annular cuff and the posterior portion are in fluid communication with each other.

13. The laryngeal mask airway device according to claim 11,
wherein the backplate is shaped so as to define an anterior laryngeal chamber region,
wherein the inflatable annular cuff is shaped so as to define, around the inflatable annular cuff an annular edge that forms an airtight seal with the anterior laryngeal chamber region, and
wherein the laryngeal mask airway device is configured such that when the inflatable balloon is disposed in free space and inflated to a pressure of 10 cm H2O:
the non-inflatable skeleton, along at least 25% of a length of a curved central axis of the inflatable annular cuff, reaches to within 2 mm of or intersects the curved central axis, and
the curved central axis being the set of all centroids of transverse cross-sectional sections of the inflatable annular cuff, wherein in each transverse cross-sectional section of the inflatable annular cuff around the inflatable annular cuff, one side of the inflatable annular cuff is defined by a straight line segment between (a) the annular edge and (b) a point on a surface of the posterior region closest to the annular edge.

14. The laryngeal mask airway device according to claim 1, wherein the inflatable balloon is shaped so as to define only the inflatable annular cuff.

15. The laryngeal mask airway device according to claim 1,
wherein the backplate is shaped so as to define an anterior laryngeal chamber region into which the backplate airway port is open, and
wherein the inflatable balloon is shaped so as to define an anterior-laryngeal-chamber-region covering portion that (a) is open to the cuff opening, (b) covers a chamber-region surface defined by the anterior laryngeal chamber region, and (c) is shaped so as to define a covering-portion opening in fluid communication with the cuff opening and the backplate airway port.

16. The laryngeal mask airway device according to claim 15, wherein the inflatable balloon forms an airtight seal between the covering-portion opening and the backplate airway port.

17. The laryngeal mask airway device according to claim 16, further comprising a balloon-restraining insert, which (a) presses the anterior-laryngeal-chamber-region covering portion of the inflatable balloon against the chamber-region surface, and (b) is disposed partially within the backplate airway port.

18. The laryngeal mask airway device according to claim 17, wherein the balloon-restraining insert is shaped so as to define a tab that is in contact with a portion of the anteriorlaryngeal-chamber-region covering portion so as to press the anterior-laryngeal-chamber-region covering portion against the chamber-region surface.

19. The laryngeal mask airway device according to claim 17,
wherein the inflatable balloon is shaped so as to define a balloon tubular portion, and
wherein the balloon-restraining insert presses the balloon tubular portion against an internal surface of the backplate airway port, such that the inflatable balloon forms the airtight seal between the covering-portion opening and the backplate airway port.

20. The laryngeal mask airway device according to claim 19, wherein the balloon-restraining insert is shaped so as to define an insert tubular portion, which presses the balloon tubular portion against the internal surface of the backplate airway port.

21. The laryngeal mask airway device according to claim 1,
wherein the non-inflatable skeleton is shaped so as to define one or more holes between the skeleton anterior side and an interior skeleton surface of the non-inflatable skeleton, and
wherein both the skeleton anterior side and the interior skeleton surface are in fluid communication with an interior of the inflatable balloon.

22. The laryngeal mask airway device according to claim 1, wherein at least a portion of the non-inflatable skeleton is shaped so as to define one or more wings, which are configured to flex with respect to the backplate when a force is applied to the wings.

23. The laryngeal mask airway device according to claim 1, wherein the non-inflatable skeleton and the backplate comprise two non-integral pieces attached together.

24. The laryngeal mask airway device according to claim 1,
wherein the backplate is shaped so as to define an anterior laryngeal chamber region and a posterior region on the other, posterior side of backplate,
wherein the inflatable annular cuff is shaped so as to define, around the inflatable annular cuff (a) a first annular edge that forms an airtight seal with the anterior laryngeal chamber region, and (b) a second annular edge that forms an airtight seal with the posterior region, and
wherein the laryngeal mask airway device is configured such that when the inflatable balloon is disposed in free space and inflated to a pressure of 10 cm H2O:
the non-inflatable skeleton, along at least 25% of a length of a curved central axis of the inflatable annular cuff, reaches to within 2 mm of or intersects the curved central axis, and
the curved central axis being the set of all centroids of transverse cross-sectional sections of the inflatable annular cuff, wherein in each transverse cross-sectional section of the inflatable annular cuff around the inflatable annular cuff, one side of the inflatable annular cuff is defined by a straight line segment between the first annular edge and the second annular edge.

25. The laryngeal mask airway device according to claim 1,
wherein the backplate is shaped so as to define an anterior laryngeal chamber region and a posterior region on the other, posterior side of backplate,
wherein the inflatable annular cuff is shaped so as to define, around the inflatable annular cuff (a) a first annular edge that forms an airtight seal with the anterior laryngeal chamber region, and (b) a second annular edge that forms an airtight seal with the posterior region, and
wherein the laryngeal mask airway device is configured such that when the inflatable balloon is disposed in free space and inflated with air to a pressure of 10 cm H2O:
along at least 25% of a length of a curved central axis of the inflatable annular cuff, no more than 75% of a cross-sectional area of the inflatable annular cuff is filled with the air, and
the curved central axis being the set of all centroids of transverse cross-sectional sections of the inflatable annular cuff, wherein in each transverse cross-sectional section of the inflatable annular cuff around the inflatable annular cuff, one side of the inflatable annular cuff is defined by a straight line segment between the first annular edge and the second annular edge.

26. The laryngeal mask airway device according to claim 1,
wherein the inflatable balloon, when disposed in free space, is characterized by a pressure-volume curve that represents the pressure in the inflatable balloon when inflated, from a deflated negative pressure, by different volumes of ambient-pressure air, which include a low-pressure volume that results in a low pressure of 10 cm H2O, wherein the pressure-volume curve includes:
a low-pressure-range average rate of change over a low-pressure volume interval between 1.0 and 1.2 times the low-pressure volume,
a medium-pressure-range average rate of change over a medium-pressure volume interval between 2.0 and 2.2 times the low-pressure volume, and
a medium pressure at a medium volume of the inflatable balloon equal to 2.0 times the low-pressure volume,
wherein the medium-pressure-range average rate of change is less than 0.5 times the low-pressure-range average rate of change, and
wherein the medium pressure is between 20 and 200 cm H2O.

27. A method comprising:
inserting a backplate, a non-inflatable skeleton, and an inflatable balloon of a laryngeal mask airway device through the mouth of a patient and disposing, at an laryngeal-mask-airway-insertion location within the throat of the patient, an inflatable annular cuff defined by the inflatable balloon, such that (a) a proximal end of an inflation tube is disposed outside the patient's mouth and (b) a proximal end of an airway tube of the laryngeal mask airway device is disposed outside the patient's mouth; and
ventilating lungs of the patient using the laryngeal mask airway device,
wherein the non-inflatable skeleton extends anteriorly from the backplate, and is shaped so as to define a skeleton anterior side that has a pre-formed shape,
wherein a distal end of the inflation tube is coupled in fluid communication with (i) an interior of the inflatable balloon for supplying air to the inflatable balloon, and (ii) at least a portion of the skeleton anterior side,
wherein a distal end of the airway tube is in fluid communication with a backplate airway port defined by the backplate,
wherein the backplate airway port is open through a cuff opening through the inflatable annular cuff, wherein the inflatable annular cuff covers at least a portion of the skeleton anterior side, and wherein the inflatable annular cuff has a cuff anterior side that is configured to form a seal around a laryngeal inlet of the patient when the inflatable annular cuff is disposed at the laryngeal-mask-airway-insertion location within the throat of the patient, wherein the laryngeal mask airway device is shaped so as to define a gastric channel having a distal gastric opening through a distal tip portion of the non-inflatable skeleton, an anterior side of the distal tip portion having an area equal to less than 20% of a total area of the skeleton anterior side, and wherein the inflatable annular cuff covers an entirety of the skeleton anterior side other than the anterior side of the distal tip portion of the non-inflatable skeleton.

* * * * *